(12) United States Patent
Lietzau et al.

(10) Patent No.: US 7,691,456 B2
(45) Date of Patent: Apr. 6, 2010

(54) SPIRO[3.3] HEPTYL-DIOXAN DERIVATIVES AND THEIR USE IN LIQUID CRYSTAL MEDIA

(75) Inventors: Lars Lietzau, Darmstadt (DE); Werner Binder, Dieburg (DE); Melanie Klasen-Memmer, Heuchelheim (DE); Eike Poetsch, Muehltal (DE); Markus Czanta, Darmstadt (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 12/089,257

(22) PCT Filed: Oct. 11, 2006

(86) PCT No.: PCT/EP2006/009791

§ 371 (c)(1),
(2), (4) Date: Apr. 4, 2008

(87) PCT Pub. No.: WO2007/045382

PCT Pub. Date: Apr. 26, 2007

(65) Prior Publication Data

US 2008/0251761 A1 Oct. 16, 2008

(30) Foreign Application Priority Data

Oct. 19, 2005 (DE) .................. 10 2005 050 080

(51) Int. Cl.
| C09K 19/34 | (2006.01) |
| C09K 19/30 | (2006.01) |
| C07C 309/06 | (2006.01) |
| C07C 31/27 | (2006.01) |
| C07C 33/05 | (2006.01) |

(52) U.S. Cl. ............. 428/1.1; 252/299.61; 252/299.63; 549/369; 568/839; 568/852

(58) Field of Classification Search .................. 428/1.1; 252/299.61, 299.63; 549/369; 568/839, 568/852

See application file for complete search history.

(56) References Cited

U.S. PATENT DOCUMENTS

| 6,790,489 B2 * | 9/2004 | Klasen-Memmer et al. .. 428/1.1 |
| 7,270,856 B2 * | 9/2007 | Taugerbeck et al. .......... 428/1.1 |
| 7,482,044 B2 * | 1/2009 | Czanta et al. ................ 428/1.3 |
| 2004/0058158 A1 | 3/2004 | Klasen-Memmer et al. |
| 2006/0022168 A1 | 2/2006 | Taugerbeck et al. |

FOREIGN PATENT DOCUMENTS

| WO | WO 2004/026991 A1 | 4/2004 |
| WO | WO 2004/050796 A1 | 6/2004 |

* cited by examiner

*Primary Examiner*—Shean C Wu
(74) *Attorney, Agent, or Firm*—Millen, White, Zelano & Branigan, P.C.

(57) ABSTRACT

The invention relates to novel dioxane derivatives of the formula $R^1\text{-}(A^1\text{-}Z^1)_m\text{-}G\text{-}(Z^2\text{-}A^2)_n\text{-}R^2$, in which G denotes (I) or (II), and in which $R^1$, $R^2$, $A^1$, $A^2$, $Z^1$, $Z^2$, m and n have the meanings indicated in claim 1, to the use thereof as component(s) of liquid-crystalline media, and to liquid-crystal and electro-optical display elements which contain the liquid-crystalline media according to the invention.

$$R^1-(A^1-Z^1)_m-G-(Z^2-A^2)_n-R^2$$

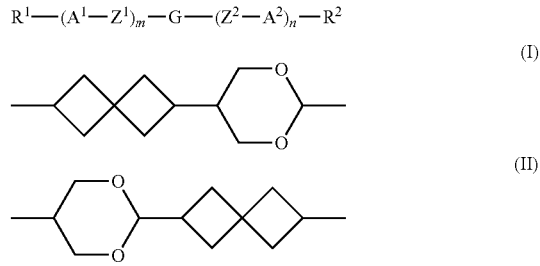

30 Claims, No Drawings

SPIRO[3.3] HEPTYL-DIOXAN DERIVATIVES AND THEIR USE IN LIQUID CRYSTAL MEDIA

The present invention relates to dioxane derivatives which contain both a dioxane ring and a spiro[3.3]heptyl group as constituent of their skeleton, to the use thereof as component(s) of liquid-crystalline media, and to liquid-crystal and electro-optical display elements which contain these liquid-crystalline media according to the invention.

The dioxane derivatives according to the invention can be used as component(s) of liquid-crystalline media, in particular for displays based on the principle of the twisted cell, the guest-host effect, the effect of deformation of aligned phases DAP or ECB (electrically controlled birefringence), the IPS effect (in-plane switching) or the effect of dynamic scattering.

All the substances employed hitherto for this purpose have certain disadvantages, for example inadequate stability to the effect of heat, light or electric fields, or unfavourable elastic and/or dielectric properties.

The invention thus had the object of finding novel stable compounds which are suitable as component(s) of liquid-crystalline media, in particular for TN, STN, IPS and TFT displays.

A further object of the present invention was to provide compounds which have low rotational viscosity, positive dielectric anisotropy AC and can be synthesised simply. In particular through the reduction in the rotational viscosity, it should be possible to achieve significantly shorter response times.

Surprisingly, it has been found that the dioxane derivatives according to the invention are eminently suitable as component(s) of liquid-crystalline media. They can be used to obtain stable liquid-crystalline media, particularly suitable for TFT or STN displays.

The physical properties of the dioxane derivatives according to the invention can be varied in broad ranges through a suitable choice of the ring members and/or the terminal substituents. Thus, for example, it is possible to obtain dioxane derivatives according to the invention having very low optical anisotropy values or low positive to highly positive dielectric anisotropy values.

In particular, the dioxane derivatives according to the invention are distinguished by low optical anisotropy values and by unexpectedly low rotational viscosities.

Liquid-crystalline media having very low optical anisotropy values are of particular importance for reflective and transflective applications, i.e. applications in which the respective LCD experiences no or only supporting backlighting.

The provision of the dioxane derivatives according to the invention very generally considerably broadens the range of liquid-crystalline substances which are suitable, from various applicational points of view, for the preparation of liquid-crystalline mixtures.

The dioxane derivatives according to the invention have a broad range of applications. Depending on the choice of the substituents, these compounds can serve as base materials of which liquid-crystalline media are predominantly composed. However, it is also possible to add liquid-crystalline base materials from other classes of compound to the dioxane derivatives according to the invention in order, for example, to influence the dielectric and/or optical anisotropy of a dielectric of this type and/or to optimise its threshold voltage and/or its viscosity.

In the pure state, the dioxane derivatives according to the invention are colourless. They are stable chemically, thermally and to light.

The present invention thus relates to dioxane derivatives of the formula I

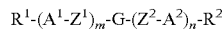

in which

G denotes

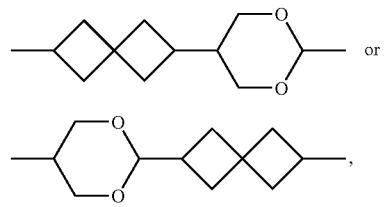

$R^1$, $R^2$ each, independently of one another, identically or differently, denote H, halogen (F, Cl, Br, I) or a linear or branched, optionally chiral alkyl or alkoxy radical having 1 to 15 C atoms which is unsubstituted, mono- or polysubstituted by halogen and in which one or more $CH_2$ groups may each be replaced, independently of one another, by —O—, —S—, —CO—, —CO—O—, —O—CO—, —O—CO—O—, —CH=CH—, —CH=CF—, —CF=CF—, —C≡C— or

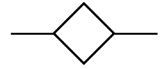

in such a way that heteroatoms are not linked directly to one another, —CN, —SCN, —NCS, —$SF_5$, —$SCF_3$, —$CF_3$, —CF=$CF_2$, —$CF_2CF_2CF_3$, —$OCF_3$, —$OCHF_2$, —$CF_2CH_2CF_3$ or —$OCH_2CF_2CHFCF_3$, $A^1$, $A^2$ each, independently of one another, identically or differently, denote a) trans-1,4-cyclohexylene, in which, in addition, one or more non-adjacent $CH_2$ groups may be replaced by —O— and/or —S— and in which, in addition, one or more H atoms may be replaced by F, b) 1,4-phenylene, in which one or two CH groups may be replaced by N and in which, in addition, one or more H atoms may be replaced by halogen (F, Cl, Br, I), —CN, —$CH_3$, —$CHF_2$, —$CH_2F$, —$CF_3$, —$OCH_3$, —$OCHF_2$ or —$OCF_3$, c) a radical from the group bicyclo[1.1.1]pentane-1,3-diyl, bicyclo[2.2.2]octane-1,4-diyl, spiro[3.3]heptane-2,6-diyl, naphthalene-2,6-diyl, naphthalene-2,7-diyl, decahydronaphthalene-2,6-diyl, 1,2,3,4-tetrahydronaphthalene-2,6-diyl, piperidine-1,4-diyl, phenanthrene-2,7-diyl, fluorene-2,7-diyl, anthracene-2,6-diyl, anthracene-2,7-diyl and indane-2,5-diyl, where one H atom or a plurality of H atoms may be replaced by halogen, in particular F, d) 1,4-cyclohexenylene or cyclobutane-1,3-diyl, $Z^1$, $Z^2$ each, independently of one another, identically or differently, denote —O—, —CH$_2$O—, —OCH$_2$—, —CO—O—, —O—CO—, —CF$_2$O—, —OCF$_2$—, —CF$_2$CF$_2$—, —CH$_2$CF$_2$—, —CF$_2$CH$_2$—, —CH$_2$CH$_2$—, —CH=CH—, —CH=CF—, —CF=CH—, —CF=CF—, —CF=CF—COO—, —O—CO—CF=CF—, —C≡C—, —CH$_2$CH$_2$CF$_2$O— or a single bond, and m, n, independently of one another, identically or differently, denote 0, 1, 2 or 3, preferably m=0, 1 or 2 and n=1 or 2, particularly preferably m=0 or 1 and n=1 or 2, and in particular m=0 and n=1 or 2.

The present invention furthermore relates to the use of compounds of the formula I as component(s) of liquid-crystalline media.

The present invention likewise relates to liquid-crystalline media having at least two liquid-crystalline components which comprise at least one compound of the formula I.

The present invention also relates to liquid-crystal display elements, in particular electro-optical display elements, which contain, as dielectric, a liquid-crystalline medium according to the invention.

Particular preference is given to reflective and transflective liquid-crystal display elements and other liquid-crystal displays of low birefringence Δn, so-called "low Δn mode displays", such as, for example, reflective and transflective TN displays.

The meaning of the formula I encompasses all isotopes of the chemical elements bound in the compounds of the formula I. In enantiomerically pure or enriched form, the compounds of the formula I are also suitable as chiral dopants and in general for achieving chiral mesophases.

Above and below, $R^1$, $R^2$, $A^1$, $A^2$, $Z^1$, $Z^2$, G, m and n have the meaning indicated, unless expressly stated otherwise. If the radicals $A^1$ and $A^2$ or $Z^1$ and $Z^2$ occur more than once, they may, independently of one another, adopt identical or different meanings.

Preferred compounds of the formula I are compounds of the sub-formula Ia

Ia and compounds of the sub-formula Ib

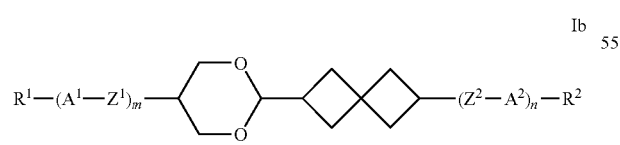

Ib in which $R^1$, $R^2$, $A^1$, $A^2$, $Z^1$, $Z^2$, m and n have the meanings indicated above.

Preference is given to compounds of the formula I in which $R^1$ denotes H or a linear alkyl radical having 1 to 10 C atoms.

Preference is likewise given to compounds of the formula I in which $R^2$ denotes H, a linear alkoxy radical having 1 to 10 C atoms, —F, —Cl, —CF$_3$, —OCF$_3$, —OCHF$_2$, —CN, —NCS or —SF$_5$, particularly preferably —F, —CF$_3$, —OCF$_3$ or —CN.

$Z^1$ preferably denotes —CH$_2$CH$_2$—, —CH=CH—, —C≡C—, —CF$_2$CF$_2$—, —CF=CF—, —CF$_2$O—, —OCF$_2$— or a single bond, particularly preferably a single bond.

$Z^2$ preferably denotes —CH$_2$CH$_2$—, —CH=CH—, —C≡C—, —CF$_2$CF$_2$—, —CF=CF—, —CF$_2$O—, —OCF$_2$— or a single bond, particularly preferably —CF$_2$O— or a single bond.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical, Bco denotes a bicyclo[2.2.2]octylene radical, Dec denotes a decahydronaphthalene-2,6-diyl radical, Nap denotes a naphthalene-2,6-diyl or naphthalene-2,7-diyl radical, Thn denotes a 1,2,3,4-tetrahydronaphthalene-2,6-diyl radical, Pip denotes a piperidine-1,4-diyl radical, Phe denotes a phenanthrene-2,7-diyl radical, Flu denotes a fluorene-2,7-diyl radical, Ant denotes an anthracene-2,6-diyl or anthracene-2,7-diyl radical and Ind denotes an indane-2,5-diyl radical, where Cyc and/or Phe may be unsubstituted or mono- or polysubstituted by CH$_3$, Cl, F or CN.

$A^1$ and $A^2$ preferably denote Phe, Cyc, Che, Pyd, Pyr or Dio, and particularly preferably Phe or Cyc.

Phe is preferably

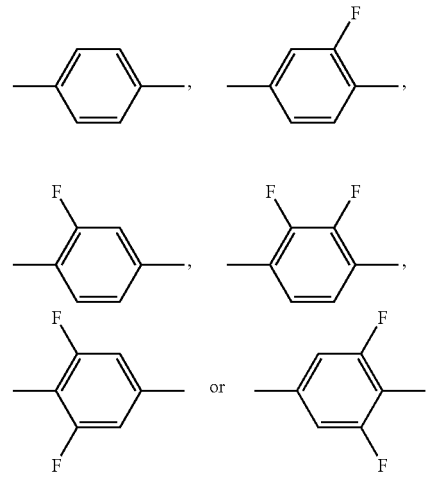

The terms 1,3-dioxane-2,5-diyl and Dio each encompass the two positional isomers

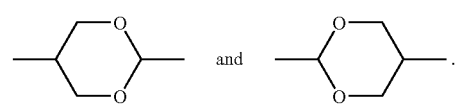

The cyclohexene-1,4-diyl group preferably has the following structures:

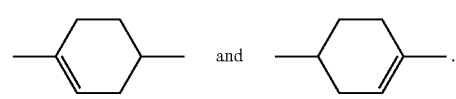

Particularly preferred compounds of the formula Ia include the following formulae:
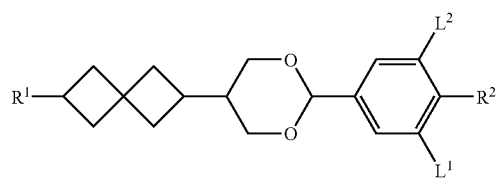
Iaa
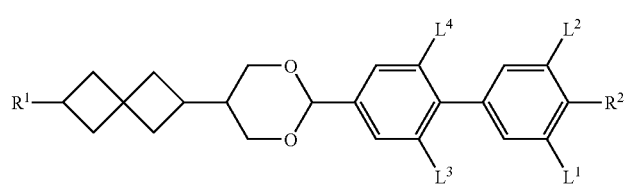
Iab
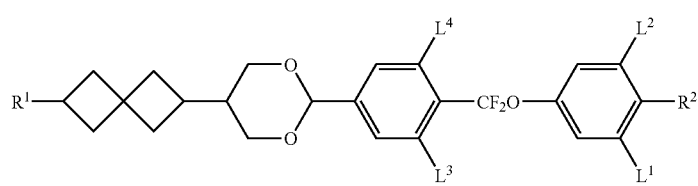
Iac
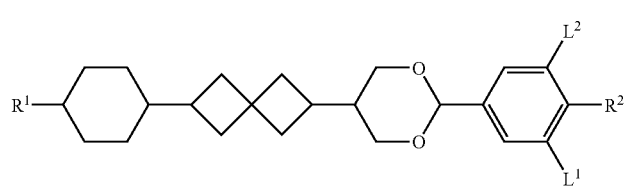
Iad
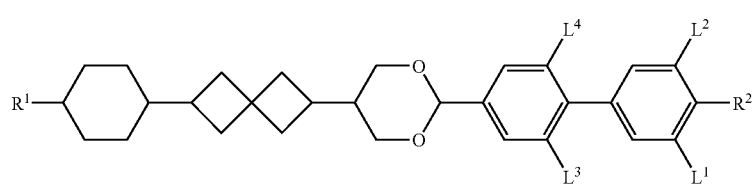
Iae
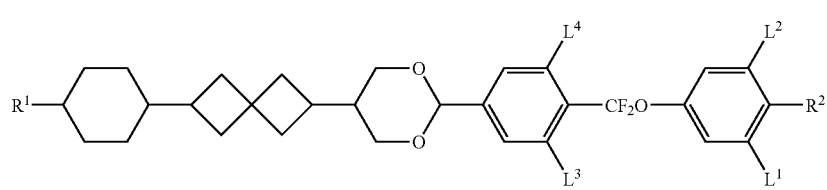
Iaf
in which $R^1$ and $R^2$ have the meanings indicated above and $L^1$, $L^2$, $L^3$ and $L^4$, independently of one another, identically or differently, denote H or F.
Particularly preferred compounds of the formula Ib include the following formulae:
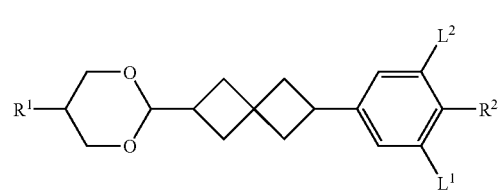
Iba -continued
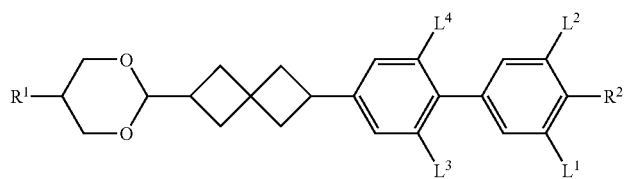
Ibb
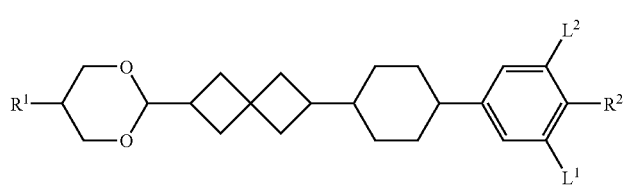
Ibc
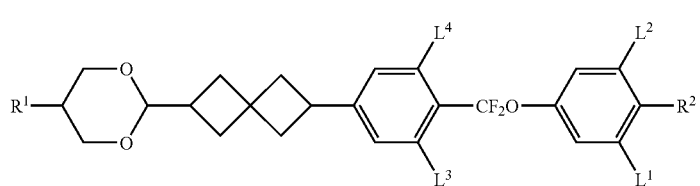
Ibd
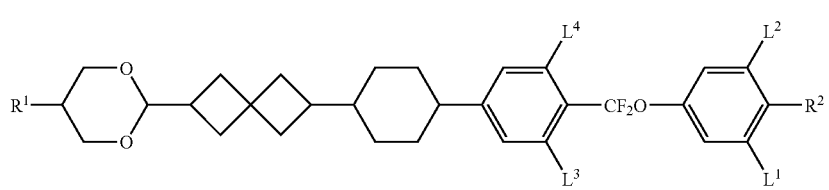
Ibe
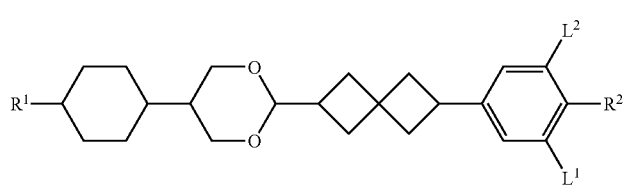
Ibf
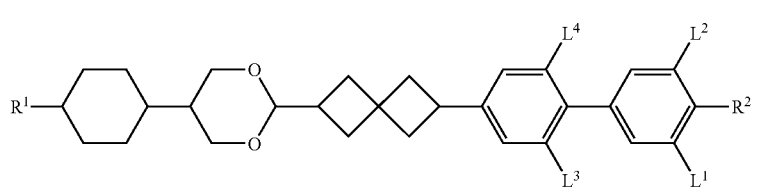
Ibg
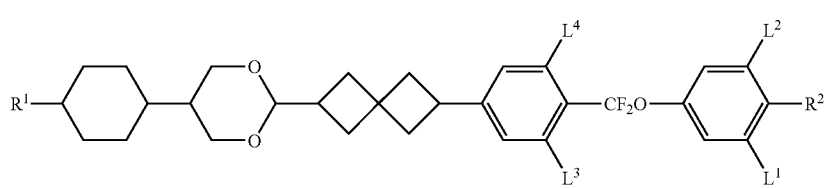
Ibh in which $R^1$ and $R^2$ have the meanings indicated above and $L^1$, $L^2$, $L^3$ and $L^4$, independently of one another, identically or differently, denote H or F.

Preference is given to compounds of the formulae Iaa to Iaf and Iba to Ibh in which $R^1$ denotes H or a linear alkyl or alkoxy radical having 1 to 10 C atoms or alkenyl or alkenyloxy having 2 to 10 C atoms.

Preference is likewise given to compounds of the formulae Iaa to Iaf and Iba to Ibh in which $R^2$ denotes —F, —$CF_3$, —$OCF_3$ or —CN.

Particular preference is given to compounds of the formulae Iaa to Iaf and Iba to Ibh in which $R^2$ denotes —F, —$CF_3$, —$OCF_3$ or —CN, $L^1$, $L^2$, $L^3$ and $L^4$, independently of one another, identically or differently, denote F or H.

Particular preference is given to compounds of the formulae Iaa and Iac. They include, in particular, the following formulae:

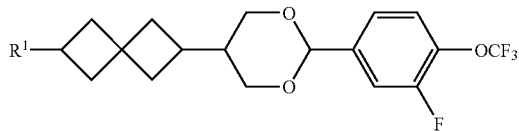
Iaa1

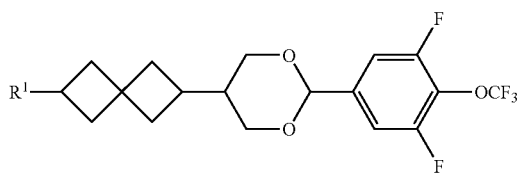
Iaa2

Iaa3
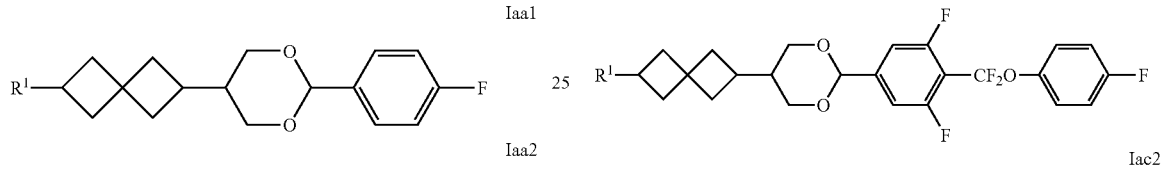

Iaa4
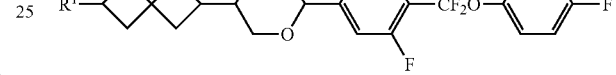

Iaa5

Iaa6

Iaa7

-continued

Iaa8

Iaa9

Iac1
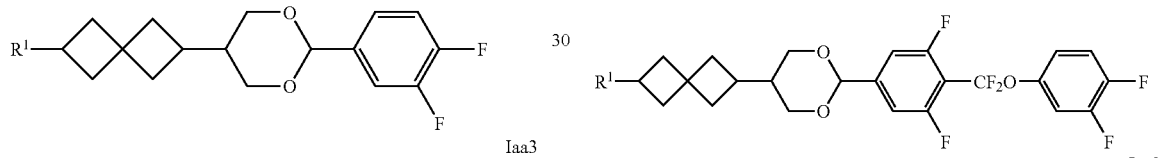

Iac2
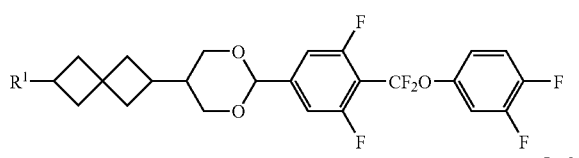

Iac3
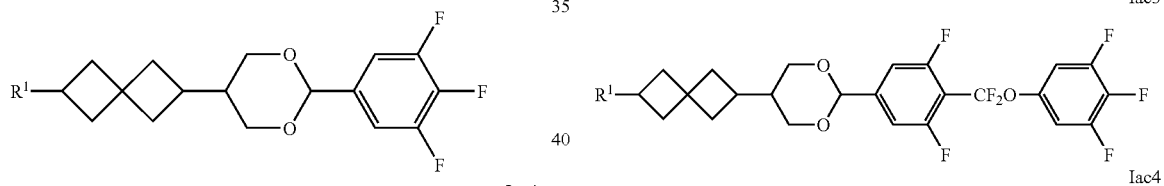

Iac4
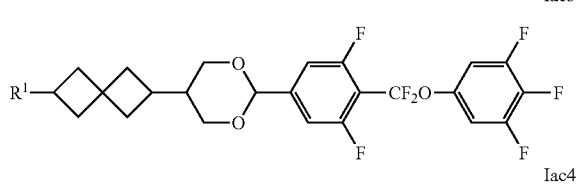

Iac5
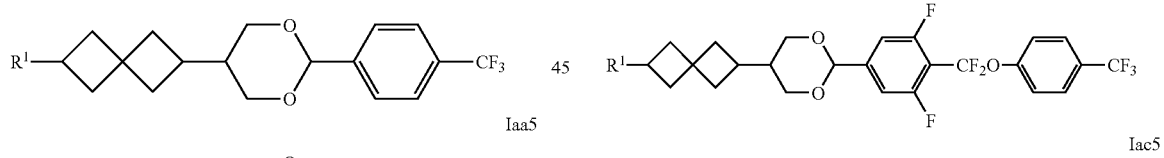

Iac6
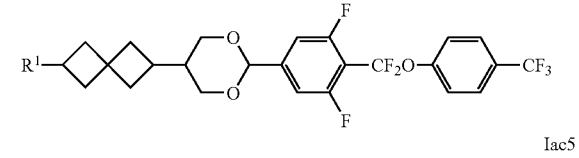

Iac7

-continued
Iac8
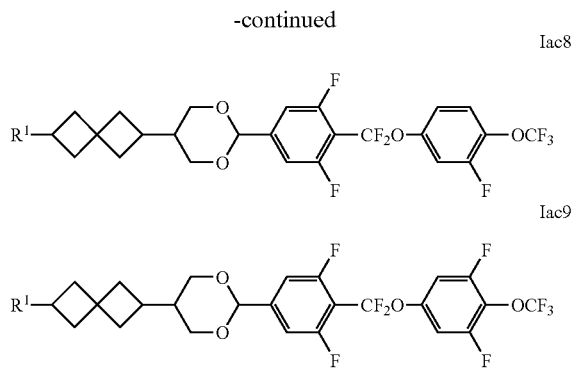
Iac9
in which R¹ has the meaning indicated above.
Particular preference is furthermore given to compounds of the formulae Iba and Ibd. They include, in particular, the following formulae:
Iba1
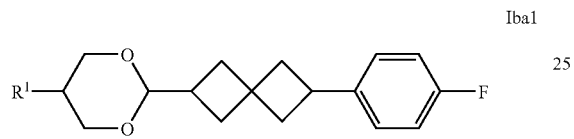
Iba2
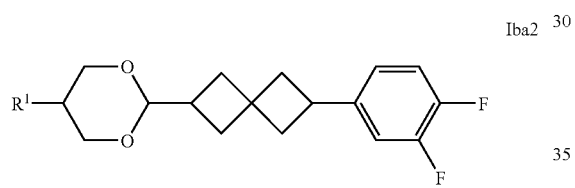
Iba3
Iba4
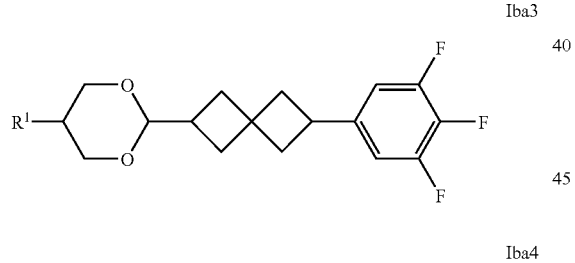
Iba5
Iba6
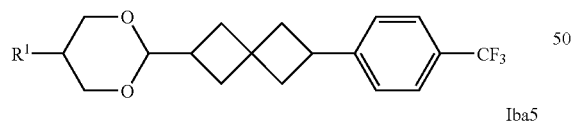
-continued
Iba7
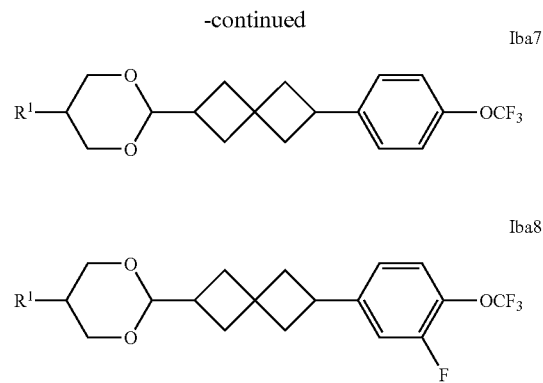
Iba8
Iba9
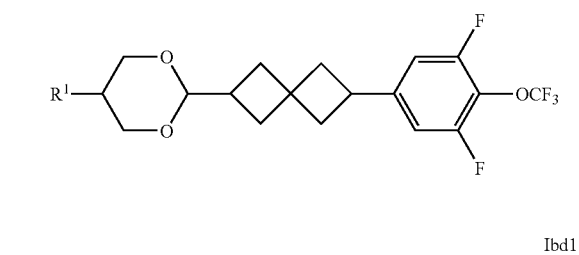
Ibd1
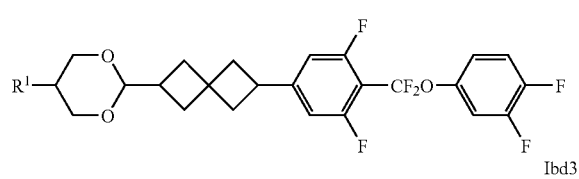
Ibd2
Ibd3
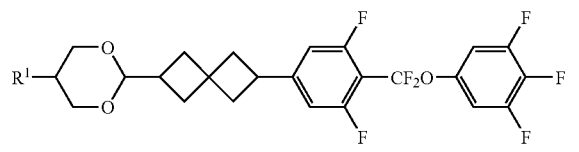
Ibd4
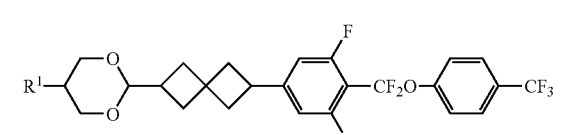
Ibd5
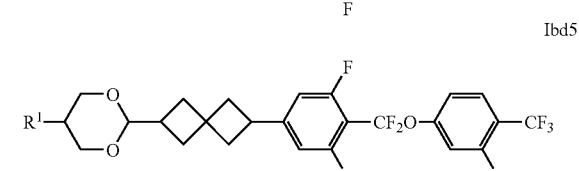
Ibd6
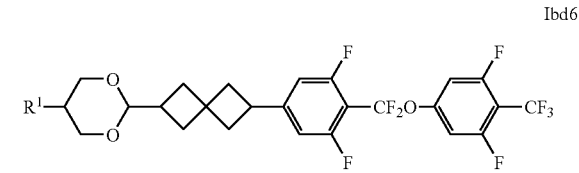

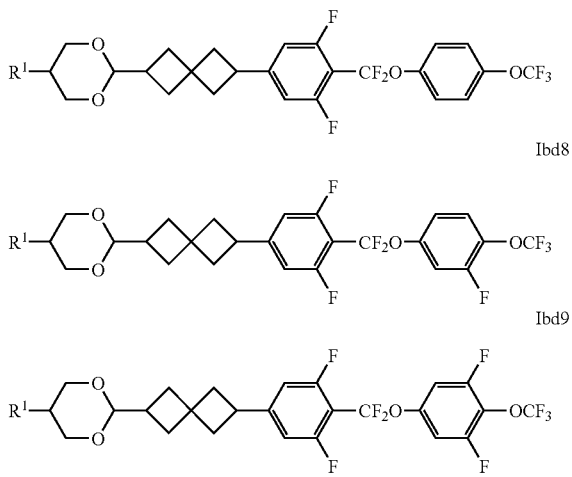

in which R¹ has the meaning indicated above.

Preference is given to compounds of the formulae Iaa1 to Iaa9, Iac1 to Iac9, Iba1 to Iba9 and Ibd1 to Ibd9 in which R¹ denotes H or a linear alkyl or alkoxy radical having 1 to 10 C atoms or alkenyl or alkenyloxy having 2 to 10 C atoms, particularly preferably a linear alkyl radical having 1 to 10 C atoms.

If R¹ and/or R² in the formulae above and below denotes an alkyl radical, this may be straight-chain or branched. It is particularly preferably straight-chain, has 2, 3, 4, 5, 6 or 7 C atoms and accordingly denotes ethyl, propyl, butyl, pentyl, hexyl or heptyl, furthermore methyl, octyl, nonyl, decyl, undecyl, dodecyl, tridecyl, tetradecyl or pentadecyl.

If R¹ and/or R² denotes an alkyl radical in which one $CH_2$ group has been replaced by —O—, this may be straight-chain or branched. It is preferably straight-chain and has 1 to 10 C atoms. The first $CH_2$ group of this alkyl radical has particularly preferably been replaced by —O—, so that the radical R¹ and/or R² attains the meaning alkoxy and denotes, in particular, methoxy, ethoxy, propoxy, butoxy, pentyloxy, hexyloxy, heptyloxy, octyloxy or nonyloxy.

Furthermore, a $CH_2$ group elsewhere may also have been replaced by —O—, so that the radical R¹ and/or R² preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R¹ and/or R² denotes an alkyl radical in which one $CH_2$ group has been replaced by —CH=CH—, this may be straight-chain or branched. It is preferably straight-chain and has 2 to 10 C atoms. Accordingly, it denotes vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl.

Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_{7-6}$-alkenyl, particularly preferably $C_2$-$C_7$-1E-alkenyl, $C_4$-$C_7$-3E-alkenyl and $C_5$-$C_7$-4-alkenyl.

Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl and 6-heptenyl. Groups having up to 5 carbon atoms are particularly preferred.

If R¹ and/or R² denotes an alkyl radical in which one $CH_2$ group has been replaced by —O— and one has been replaced by —CO—, these are preferably adjacent. These thus contain an acyloxy group —CO—O— or an oxycarbonyl group —O—CO—. These are particularly preferably straight-chain and have 2 to 6 C atoms.

Accordingly, they denote in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R¹ and/or R² denotes an alkyl radical in which one $CH_2$ group has been replaced by unsubstituted or substituted —CH=CH— and an adjacent $CH_2$ group has been replaced by —CO—, —CO—O— or —O—CO—, this may be straight-chain or branched. It is preferably straight-chain and has 4 to 13 C atoms. Accordingly, it particularly preferably denotes acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R¹ and/or R² denotes an alkyl or alkenyl radical which is monosubstituted by CN or $CF_3$, this radical is preferably straight-chain and substitution by CN or $CF_3$ is in the ω-position.

If R¹ and/or R² denotes an alkyl radical which is at least monosubstituted by halogen, this radical is preferably straight-chain. Halogen is preferably F or Cl. In the case of polysubstitution, halogen is preferably F. The resultant radicals also include perfluorinated radicals. In the case of monosubstitution, the fluorine or chlorine substituent can be in any desired position, but is preferably in the ω-position.

Compounds of the formula I having a branched wing group R¹ and/or R² may occasionally be of importance owing to better solubility in the conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals R¹ and/or R² are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

Formula I covers both the racemates of these compounds and the optical antipodes, and mixtures thereof.

Of the compounds of the formula I and the sub-formulae, preference is given to those in which at least one of the radicals present therein has one of the preferred meanings indicated.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se, which are not mentioned here in greater detail.

The compounds of the formula I can be prepared, for example, in accordance with the following reaction schemes or analogously thereto. Further synthetic methods are given in the examples.

Scheme 1:

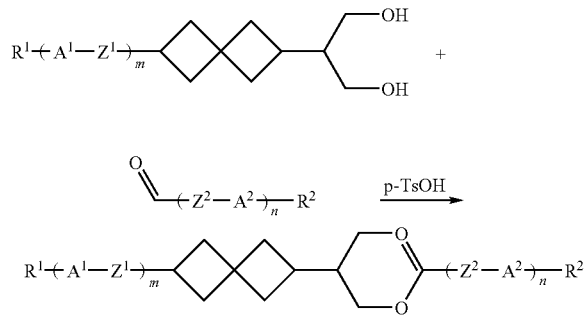

Scheme 2:

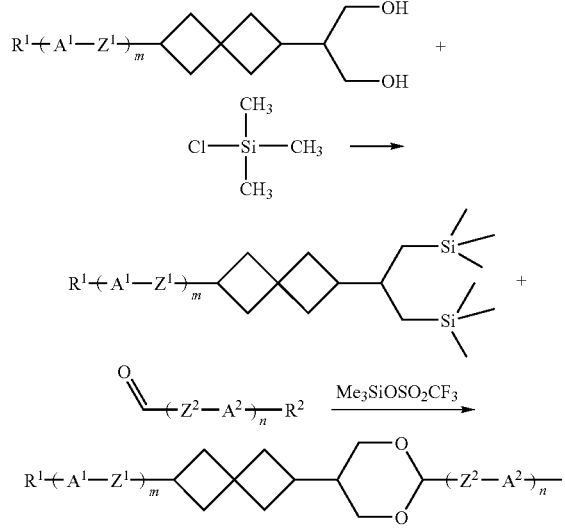

Scheme 3:

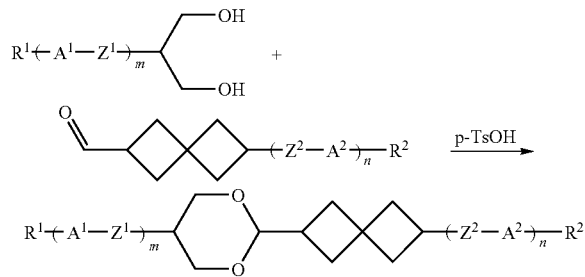

In Schemes 1 to 3, $R^1$, $R^2$, $A^1$, $A^2$, $Z^1$, $Z^2$, m and n have the meaning indicated above.

The present invention likewise relates to the spirodiols of the following formula

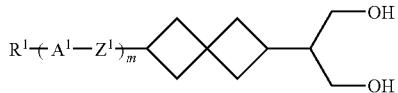

in which $R^1$, $A^1$, $Z^1$ and m have the meanings indicated in relation to formula I, which are employed as starting materials in Schemes 1 and 2.

The other starting materials are either known or can be prepared analogously to known compounds.

If desired, the starting materials can also be formed in situ by not isolating them from the reaction mixture, but instead immediately converting them further into the compounds of the formula I.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of the media according to the invention can be characterised by the formulae 1, 2, 3, 4 and 5:

| R'-L-E-R'' | 1 |
| R'-L-COO-E-R'' | 2 |
| R'-L-OOC-E-R'' | 3 |
| R'-L-CH$_2$CH$_2$-E-R'' | 4 |
| R'-L-C≡C-E-R'' | 5 |

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group Cyc, Phe and Pyr and simultaneously one or more components selected from the compounds of the formulae 1, 2, 3, 4 and 5 in which one of the radicals L and E is selected from the group Cyc, Phe and Pyr and the other radical is selected from the group -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group -Phe-Cyc-, -Cyc-Cyc-, -G-Phe- and -G-Cyc-.

R' and/or R" each, independently of one another, denote alkyl, alkenyl, alkoxy, alkoxyalkyl, alkenyloxy or alkanoyloxy having up to 8 C atoms, —F, —Cl, —CN, —NCS, —(O)$_i$CH$_{3-(k+l)}$F$_k$Cl$_l$, where i is 0 or 1, k and l, independently of one another, identically or differently, are 0, 1, 2 or 3, and the following applies to the sum (k+l): $1 \leq (k+l) \leq 3$.

In a smaller sub-group of the compounds of the formulae 1, 2, 3, 4 and 5, R' and R" each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is known as group B, R" denotes —F, —Cl, —NCS or —(O)$_i$CH$_{3-(k+l)}$F$_k$Cl$_l$, where i is 0 or 1, k and l, independently of one another, identically or differently, are 0, 1, 2 or 3, and the following applies to the sum (k+l): $1 \leq (k+l) \leq 3$. The compounds in which R" has this meaning are referred to by the sub-formulae 1b, 2b, 3b, 4b and 5b. Particular preference is given to those compounds of the sub-formulae 1b, 2b, 3b, 4b and 5b in which R" has the meaning —F, —Cl, —NCS, —CF$_3$, —OCHF$_2$ or —OCF$_3$.

In the compounds of the sub-formulae 1b, 2b, 3b, 4b and 5b, R' has the meaning indicated for the compounds of the sub-formulae 1a to 5a and is preferably alkyl, alkenyl, alkoxy or alkoxyalkyl.

In a further smaller sub-group of the compounds of the formulae 1, 2, 3, 4 and 5, R" denotes —CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meaning indicated for the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:

group A: preferably 0 to 90%, particularly preferably 20 to 90%, in particular 30 to 90%;
group B: preferably 0 to 80%, particularly preferably 10 to 80%, in particular 10 to 65%;
group C: preferably 0 to 80%, particularly preferably 5 to 80%, in particular 5 to 50%;

where the sum of the proportions by weight of the group A, B and/or C compounds present in the respective media according to the invention is preferably 5 to 90% and particularly preferably 10 to 90%.

The media according to the invention preferably comprise 1 to 40%, particularly preferably 5 to 30%, of the compounds of the formula I according to the invention. Preference is furthermore given to media comprising more than 40%, particularly preferably 45 to 90%, of compounds of the formula I according to the invention. The media preferably comprise three, four or five compounds according to the invention.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0 to 15%, preferably 0 to 10%, of pleochroic dyes and/or chiral dopants can be added. The individual compounds added are preferably employed in concentrations of 0.01 to 6%, particularly preferably 0.1 to 3%. However, the concentration data of the other constituents of the liquid-crystal mixtures, i.e. the liquid-crystalline or mesogenic compounds, are indicated here without taking into account the concentration of these additives.

The following examples are intended to explain the invention without limiting it. Above and below, percentage data denote percent by weight. All temperatures are given in degrees Celsius. m.p. denotes melting point and cl.p.=clearing point. Furthermore, C=crystalline state, N=nematic phase, Sm=smectic phase and I=isotropic phase. The data between these symbols represent the transition temperatures. $\Delta n$ denotes optical anisotropy (589 nm, 20° C.), and $\Delta \varepsilon$ the dielectric anisotropy (1 kHz, 20° C.).

The $\Delta n$ and $\Delta \varepsilon$ values of the compounds according to the invention are obtained by extrapolation from liquid-crystalline mixtures which consist of 10% of the respective compound according to the invention and 90% of the commercially available liquid crystal ZLI 4792 (Merck, Darmstadt).

"Conventional work-up" means: water is added if necessary, the mixture is extracted with methylene chloride, diethyl ether or toluene, the phases are separated, the organic phase is dried and evaporated, and the product is purified by distillation under reduced pressure or crystallisation and/or chromatography.

Above and below, the following abbreviations are used:

| | |
|---|---|
| DCM | dichloromethane |
| DMF | dimethylformamide |
| MTB-Ether | methyl tert-butyl ether |

| | |
|---|---|
| RT | room temperature (about 20° C.) |
| THF | tetrahydrofuran |

EXAMPLES

Example 1

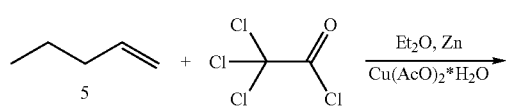

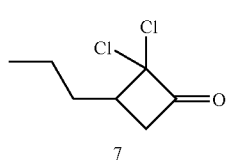

346 ml (3.00 mol) of 1-pentene are dissolved in 3 l of diethyl ether, and 315 g (4.83 mol) of zinc and 15 g (80 mmol) of copper(II) acetate monohydrate are added. 370 ml (3.30 mol) of trichloroacetyl chloride are subsequently added dropwise to the batch, during which the reaction mixture begins to boil. After 24 hours at room temperature, the solids are separated off, and the filtrate is washed with water, evaporated and passed through silica gel (pentane/DCM 3:2), giving 365 g of a yellow oil (content: 64%).

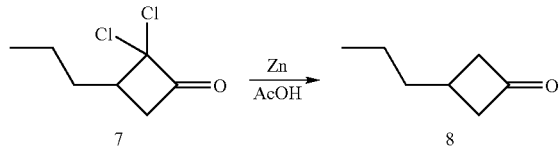

430 mmol of the chlorinated cyclobutanone 7 (100 g (content 77%)) are dissolved in 500 ml of acetic acid, and 100 g (1.5 mol) of zinc are added in portions at such a rate that a temperature of 80° C. is not exceeded. When the addition is complete, the batch is held at 80° C. for a further 2 hours. After cooling to room temperature, the batch is stirred with 500 ml of water and extracted with MTB ether. The combined organic phases are washed with water and saturated sodium hydrogencarbonate solution, dried over sodium sulfate and evaporated, giving 45.1 g of a yellow oil (content 78.7%).

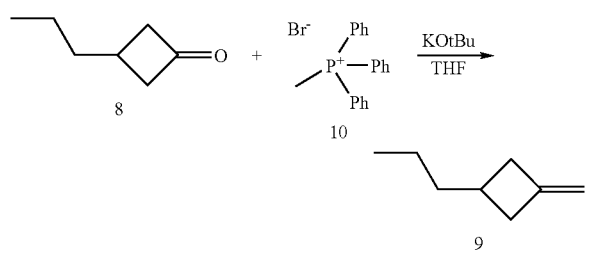

930 g (2.6 mol) of the Wittig salt 10 and 292 g of the ketone 8 are suspended in 2.5 l of THF, and 292 g (2.6 mol) of potassium tert-butoxide are added in portions at a temperature below 20° C. The batch is stirred overnight at room temperature. After addition of water, the mixture is acidified using hydrochloric acid and extracted with n-pentane. The organic phase is evaporated and filtered through silica gel with n-pentane, giving 100.7 g (content 30%) of a yellow liquid.

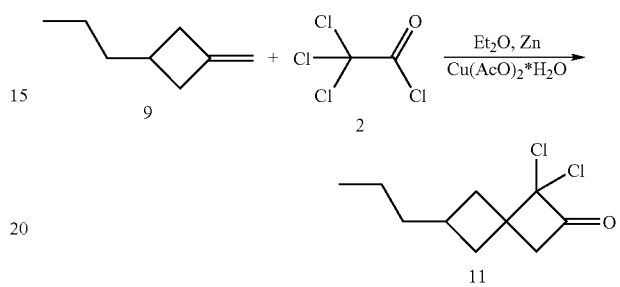

The ketone 11 is prepared analogously to the above procedure.

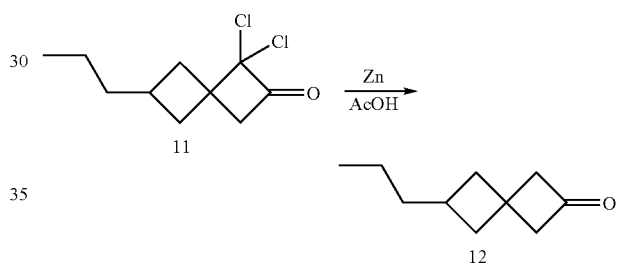

The dechlorination to give the ketone 12 is carried out analogously to the above procedure.

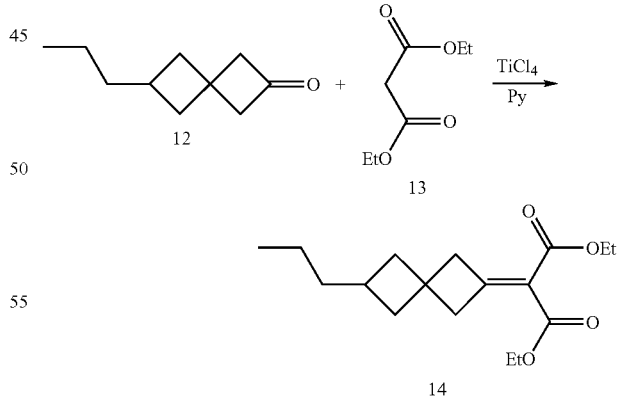

30.0 ml (273 mmol) of titanium tetrachloride are added to 100 ml of THF and 300 ml of dichloromethane at a temperature of −10° C. to −2° C. 22.8 ml (150 mmol) of diethyl malonate (13) and 24.0 g (95%, 150 mmol) of the ketone 12 are subsequently added to the reaction solution at −10° C. 44.0 ml (546 mmol) of pyridine are added dropwise to the batch at a temperature below −5° C. After 18 hours at room temperature, 1500 ml of water are added to the reaction mixture. The organic phase is washed with water and evaporated. The residue is filtered through silica gel (toluene/MTB ether 9:1), giving 45.3 g (89% purity; 91%) of the ester 14.

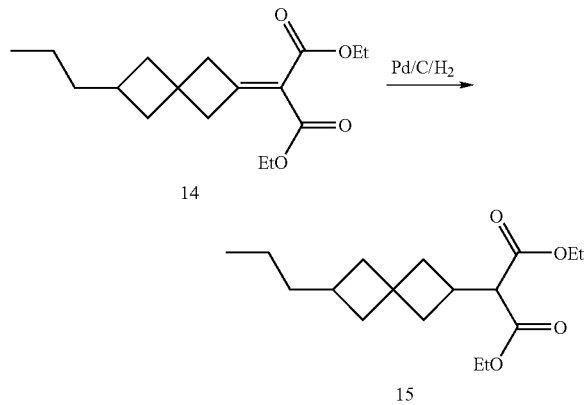

45.3 g (90% purity, 140 mmol) of the diester 14 are hydrogenated on a palladium catalyst in THF. The catalyst is separated off, and the solution is evaporated. The residue obtained is employed in the next step without further purification. 44.4 g (92% purity) of the saturated ester 15 are obtained.

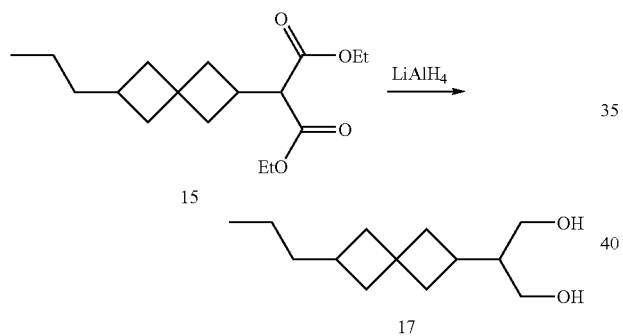

A solution of 44.4 g (150 mmol) of the diester 15 in 100 ml of THF is added under nitrogen to a suspension of 6.3 g (170 mmol) of lithium aluminium hydride in 100 ml of THF. During this addition, the batch warms to the boil. When the addition is complete, the batch is heated under reflux for 1 hour. The batch is carefully hydrolysed using water and hydrochloric acid at room temperature. The reaction mixture is filtered through Celite. The organic phase is washed with water and saturated sodium hydrogencarbonate solution and evaporated, giving 32.1 g (content 77.4%) of the diol 17.

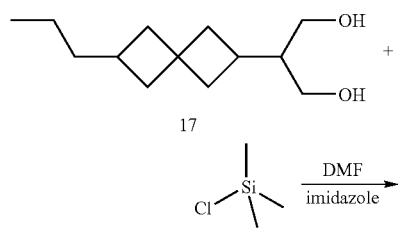

-continued

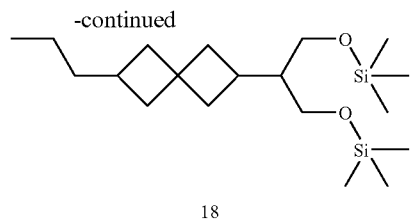

8.0 g (77.4% purity, 29.1 mmol) of the diol 17 and 9.0 g (132 mmol) of imidazole are dissolved in 60 ml of DMF under nitrogen, 11.4 ml (90.0 mmol) of chlorotrimethylsilane are added, and the mixture is stirred overnight. Water is added to the batch, which is then extracted with MTB ether. The organic phase is evaporated, and the residue is purified over silica gel, giving 5.5 g (90%) of the silyl ether 18.

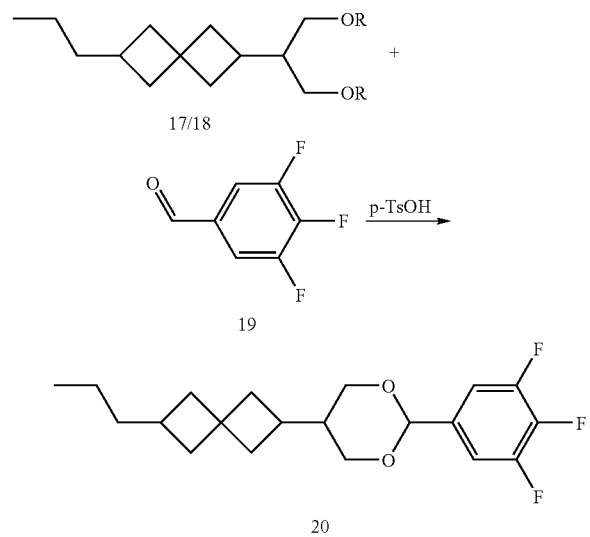

Synthetic route a), R=H, 16.0 g (77.4% purity, 58.3 mmol) of the diol 17 and 9.3 g (58.0 mmol) of the aldehyde 19 are dissolved in 100 ml of toluene, 400 mg of p-toluenesulfonic acid (p-TsOH) are added, and the mixture is heated under reflux on a water separator. The batch is subsequently washed with water and saturated sodium hydrogencarbonate solution, evaporated and passed through silica gel (toluene/heptane). The product obtained is crystallised from heptane, giving 5.7 g of the dioxane 20 as colourless crystals of melting point 58° C.

Synthetic Route b), R=SiMe$_3$:

0.4 ml (2.1 mmol) of trimethylsilyl trifluoromethanesulfonate is added under nitrogen to a solution of 5.0 g (14.2 mmol) of the disilyl ether 18 in 60 ml of dichloromethane at −78° C. A solution of 3.2 g (20.0 mmol) of the aldehyde 19 is subsequently added dropwise. After 2 hours at the low temperature, 2.0 ml of pyridine are added, and the cooling is removed. After addition of 70 ml of saturated sodium hydrogencarbonate solution, the aqueous phase is extracted with dichloromethane, and the combined organic phases are dried over sodium sulfate and evaporated. The further purification is carried out in the manner described in synthetic route a), giving 3.2 g (64%) of compound 20.

C 58 I,

Δε=13.9 and

Δn=0.0615.

The following compounds according to the invention are obtained analogously to Example 1 using the corresponding precursors:

Examples 2-18

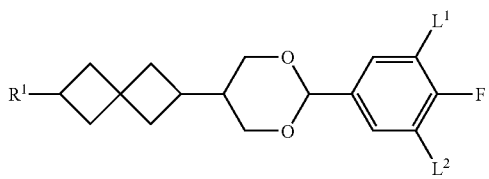

Examples 19-36

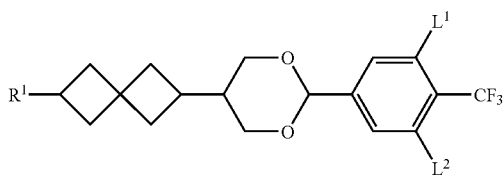

Examples 37-54

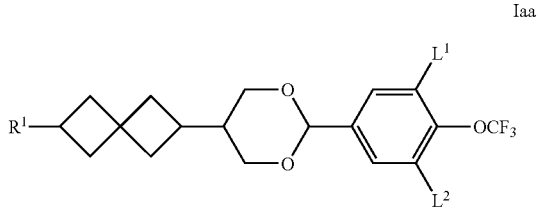

Examples 55-72

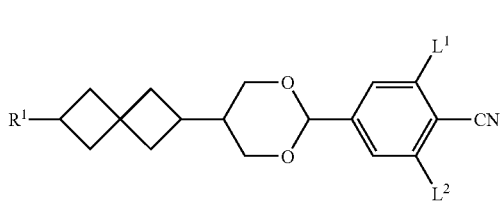

| Examples | | | | $R^1$ | $L^1$ | $L^2$ |
|---|---|---|---|---|---|---|
| 1. | 19. | 37. | 55. | $C_3H_7$ | F | F |
| 2. | 20. | 38. | 56. | $C_3H_7$ | H | F |
| 3. | 21. | 39. | 57. | $C_3H_7$ | H | H |
| 4. | 22. | 40. | 58. | $C_2H_5$ | H | H |
| 5. | 23. | 41. | 59. | $C_2H_5$ | H | F |
| 6. | 24. | 42. | 60. | $C_2H_5$ | F | F |
| 7. | 25. | 43. | 61. | $C_4H_9$ | H | H |
| 8. | 26. | 44. | 62. | $C_4H_9$ | H | F |
| 9. | 27. | 45. | 63. | $C_4H_9$ | F | F |
| 10. | 28. | 46. | 64. | $C_5H_{11}$ | H | H |
| 11. | 29. | 47. | 65. | $C_5H_{11}$ | H | F |
| 12. | 30. | 48. | 66. | $C_5H_{11}$ | F | F |
| 13. | 31. | 49. | 67. | $C_6H_{13}$ | H | H |
| 14. | 32. | 50. | 68. | $C_6H_{13}$ | H | F |
| 15. | 33. | 51. | 69. | $C_6H_{13}$ | F | F |
| 16. | 34. | 52. | 70. | $C_7H_{15}$ | H | H |
| 17. | 35. | 53. | 71. | $C_7H_{15}$ | H | F |
| 18. | 36. | 54. | 72. | $C_7H_{15}$ | F | F |

The following compound according to the invention is obtained analogously to Example 1 using the corresponding precursor:

Example 73

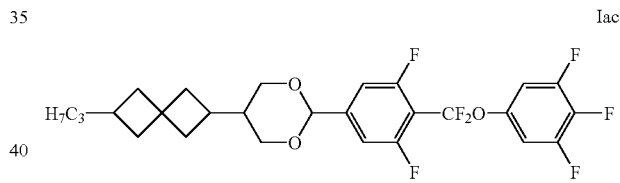

C 66 N (63.4) I,

Δε=24.3 and

Δn=0.0797.

The following compounds according to the invention are obtained analogously to Example 73 using the corresponding precursors:

Examples 74-90

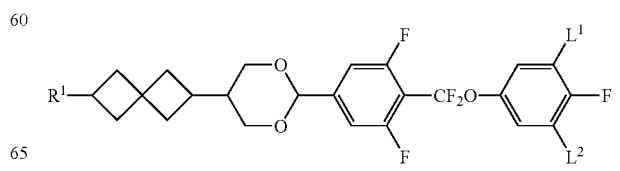

Examples 91-108

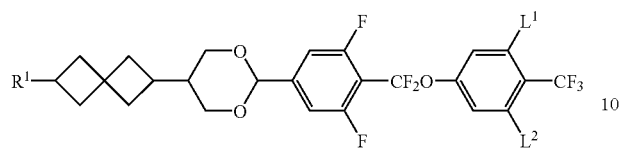

Examples 109-126

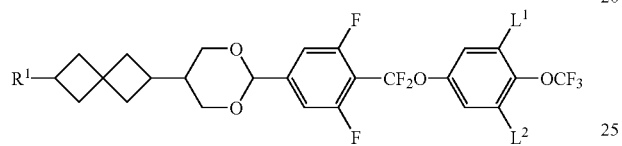

Examples 127-144

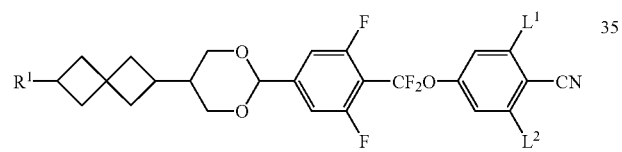

| Examples | | | | R¹ | L¹ | L² |
|---|---|---|---|---|---|---|
| 73. | 91. | 109. | 127. | C₃H₇ | F | F |
| 74. | 92. | 110. | 128. | C₃H₇ | H | F |
| 75. | 93. | 111. | 129. | C₃H₇ | H | H |
| 76. | 94. | 112. | 130. | C₂H₅ | H | H |
| 77. | 95. | 113. | 131. | C₂H₅ | H | F |
| 78. | 96. | 114. | 132. | C₂H₅ | F | F |
| 79. | 97. | 115. | 133. | C₄H₉ | H | H |
| 80. | 98. | 116. | 134. | C₄H₉ | H | F |
| 81. | 99. | 117. | 135. | C₄H₉ | F | F |
| 82. | 100. | 118. | 136. | C₅H₁₁ | H | H |
| 83. | 101. | 119. | 137. | C₅H₁₁ | H | F |
| 84. | 102. | 120. | 138. | C₅H₁₁ | F | F |
| 85. | 103. | 121. | 139. | C₆H₁₃ | H | H |
| 86. | 104. | 122. | 140. | C₆H₁₃ | H | F |
| 87. | 105. | 123. | 141. | C₆H₁₃ | F | F |
| 88. | 106. | 124. | 142. | C₇H₁₅ | H | H |
| 89. | 107. | 125. | 143. | C₇H₁₅ | H | F |
| 90. | 108. | 126. | 144. | C₇H₁₅ | F | F |

For Examples 78 and 109, the following properties are determined:

TABLE 1

| Example | Phase range | Δε | Δn |
|---|---|---|---|
| 78 | C 71 N (50.5) I | 23.9 | 0.0894 |
| 109 | C 77 N 82.0 I | 25.4 | 0.0934 |

Example 145

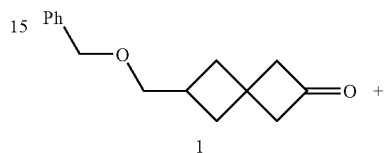

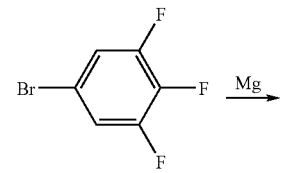

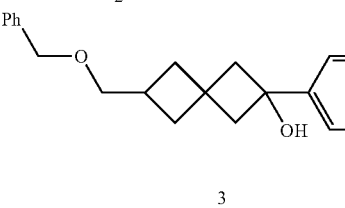

The corresponding Grignard reagent is prepared from 3.2 g (130 mmol) of magnesium turnings and 15.5 ml (130 mmol) of the bromide 2 in 75 ml of THF under nitrogen. A solution of the ketone 1 in 25 ml of THF is subsequently added to the reagent. The batch is heated at the boil for 1 hour. The cooled batch is hydrolysed, adjusted to pH 1 using hydrochloric acid and extracted with MTB ether. The organic phase is washed with saturated sodium hydrogencarbonate solution and evaporated. The residue obtained is purified on silica gel (toluene).

Yield: 22.0 g (68%)

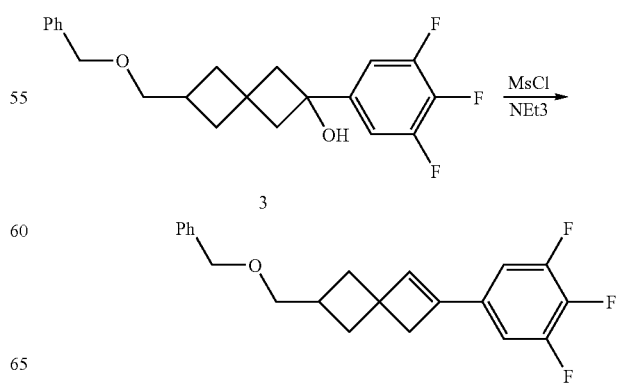

Under nitrogen, 14.4 g (40.0 mmol) of the alcohol 3 are dissolved in 80 ml of dichloromethane and 17 ml of triethylamine, and 4.1 ml (53.4 mmol) of methanesulfonyl chloride (MsCl) are added at 0° C. The batch is stirred overnight at room temperature. The reaction mixture is subsequently added to water and diluted with n-heptane. The organic phase is evaporated, and the residue obtained is passed through silica gel. The residue is employed in the following step without further purification.

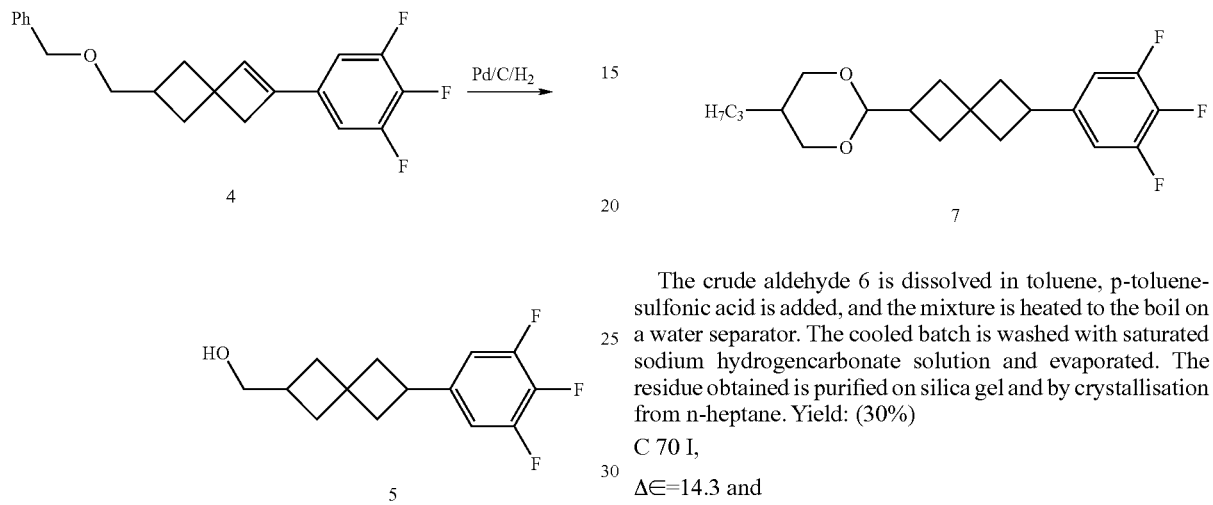

13.9 g of the crude alkene 4 are dissolved in THF and hydrogenated on a palladium catalyst. The hydrogenation solution is evaporated, and the residue obtained is purified on silica gel. Yield: 9.7 g (88%)

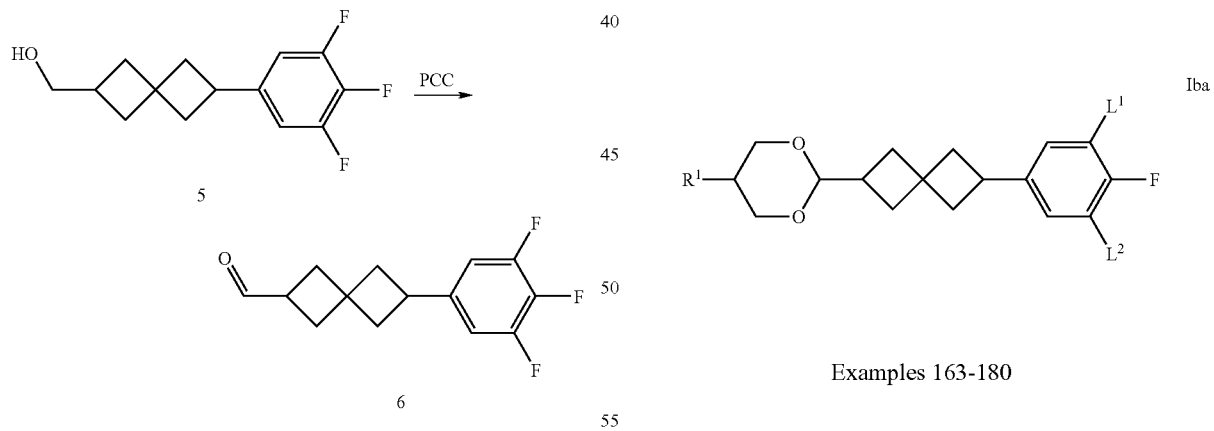

Under nitrogen, a solution of 9.4 g (36.7 mmol) of the alcohol 5 in 60 ml of DCM is added to 9.6 g (44.4 mmol) of pyridinium chlorochromate (PCC), 1.2 g of sodium acetate and 6 g of Celite suspended in 50 ml of dichloromethane. When the reaction is complete, the solid is separated off and washed with DCM. The eluate is washed with 1 N sodium hydroxide solution and 2 N hydrochloric acid and evaporated. The residue obtained is passed through silica gel. The residue is employed in the subsequent step without further purification.

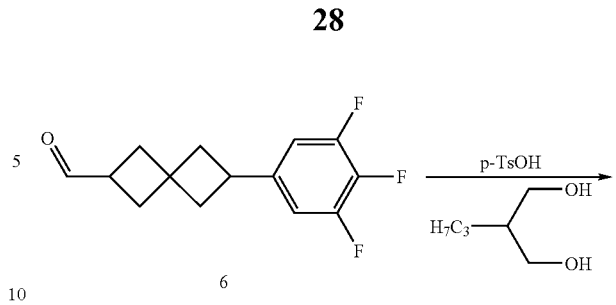

The crude aldehyde 6 is dissolved in toluene, p-toluenesulfonic acid is added, and the mixture is heated to the boil on a water separator. The cooled batch is washed with saturated sodium hydrogencarbonate solution and evaporated. The residue obtained is purified on silica gel and by crystallisation from n-heptane. Yield: (30%)

C 70 I, $\Delta\varepsilon$=14.3 and $\Delta$n=0.0322.

The following compounds according to the invention are obtained analogously to Example 145 using the corresponding precursors:

Examples 146-162

Iba

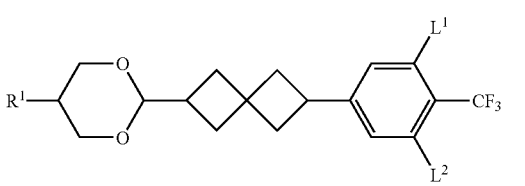

Examples 163-180

Iba

Examples 181-198
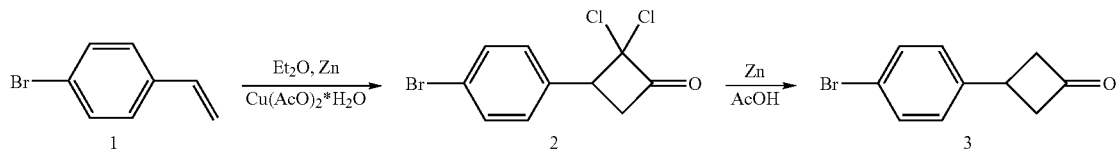
Examples 199-216
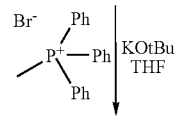
| Examples | | | | R[1] | L[1] | L[2] |
|---|---|---|---|---|---|---|
| 145. | 163. | 181. | 199. | $C_3H_7$ | F | F |
| 146. | 164. | 182. | 200. | $C_3H_7$ | H | F |
| 147. | 165. | 183. | 201. | $C_3H_7$ | H | H |
| 148. | 166. | 184. | 202. | $C_2H_5$ | H | H |
| 149. | 167. | 185. | 203. | $C_2H_5$ | H | F |
| 150. | 168. | 186. | 204. | $C_2H_5$ | F | F |
| 151. | 169. | 187. | 205. | $C_4H_9$ | H | H |
| 152. | 170. | 188. | 206. | $C_4H_9$ | H | F |
| 153. | 171. | 189. | 207. | $C_4H_9$ | F | F |
| 154. | 172. | 190. | 208. | $C_5H_{11}$ | H | H |
| 155. | 173. | 191. | 209. | $C_5H_{11}$ | H | F |
| 156. | 174. | 192. | 210. | $C_5H_{11}$ | F | F |
| 157. | 175. | 193. | 211. | $C_6H_{13}$ | H | H |
| 158. | 176. | 194. | 212. | $C_6H_{13}$ | H | F |
| 159. | 177. | 195. | 213. | $C_6H_{13}$ | F | F |
| 160. | 178. | 196. | 214. | $C_7H_{15}$ | H | H |
| 161. | 179. | 197. | 215. | $C_7H_{15}$ | H | F |
| 162. | 180. | 198. | 216. | $C_7H_{15}$ | F | F |
The compound of Example 201 is obtained as follows.
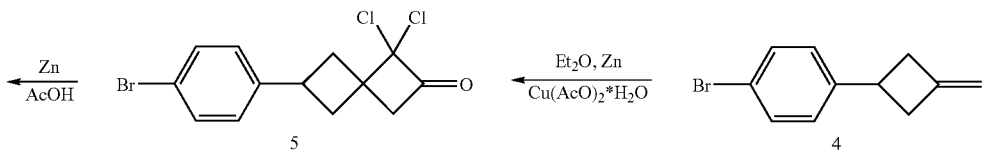
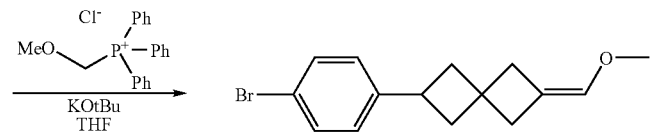
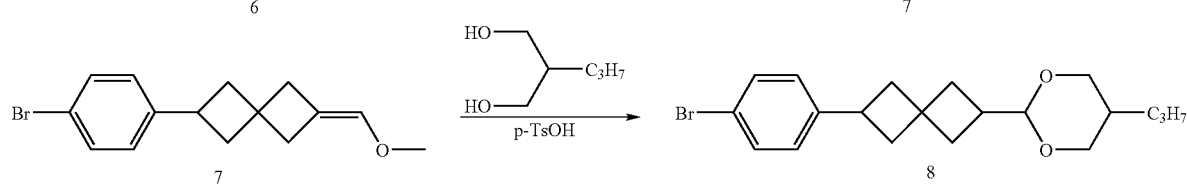

100 ml of toluene are added to 24.8 g (85 mmol) of the enol ether 7.10 g (85 mmol) of 2-propyl-1,3-propanediol and 400 mg of p-toluenesulfonic acid, and the mixture is heated at the boil for 3 h on a water separator. The cooled batch is washed with sat. NaHCO$_3$ soln. and evaporated. The crystals forming in the residue are isolated.

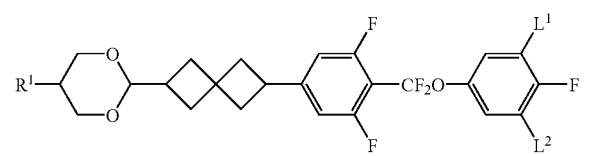

8

9

15 ml of N-methylpyrrolidone are added to 3.7 g (9.8 mmol) of the bromide 8 and 1.1 g (12.6 mmol) of copper cyanide, and the mixture is warmed at 140° C. for 4 h. 100 ml of water are added to the cooled batch, which is then extracted with MTB ether. The organic phase is filtered, dried and evaporated. After crystallisation from ethanol at −20° C., the final purification is carried out by means of HPLC.

The product has the following properties:

C 69 S$_H$ (53) N 73.4 I,

Δ∈=26.2 and

Δn=0.1120.

Examples 217-234

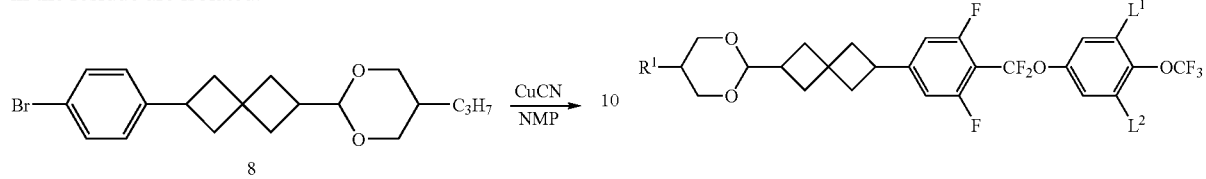

Ibd

Examples 235-252

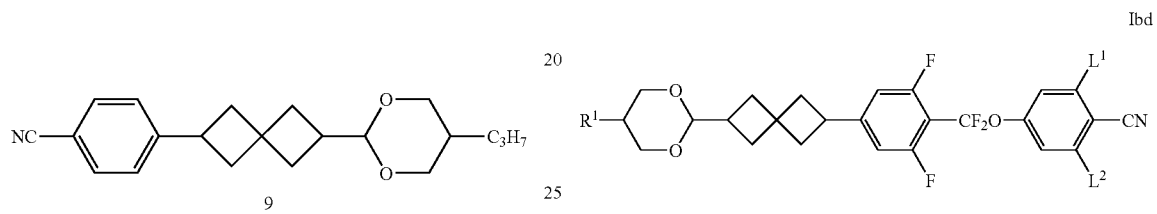

Ibd

Examples 253-270

Ibd

Examples 271-288

Ibd

| | Examples | | | R$^1$ | L$^1$ | L$^2$ |
|---|---|---|---|---|---|---|
| 217. | 235. | 253. | 271. | C$_3$H$_7$ | F | F |
| 218. | 236. | 254. | 272. | C$_3$H$_7$ | H | F |
| 219. | 237. | 255. | 273. | C$_3$H$_7$ | H | H |
| 220. | 238. | 256. | 274. | C$_2$H$_5$ | H | H |
| 221. | 239. | 257. | 275. | C$_2$H$_5$ | H | F |
| 222. | 240. | 258. | 276. | C$_2$H$_5$ | F | F |
| 223. | 241. | 259. | 277. | C$_4$H$_9$ | H | H |
| 224. | 242. | 260. | 278. | C$_4$H$_9$ | H | F |
| 225. | 243. | 261. | 279. | C$_4$H$_9$ | F | F |
| 226. | 244. | 262. | 280. | C$_5$H$_{11}$ | H | H |
| 227. | 245. | 263. | 281. | C$_5$H$_{11}$ | H | F |
| 228. | 246. | 264. | 282. | C$_5$H$_{11}$ | F | F |
| 229. | 247. | 265. | 283. | C$_6$H$_{13}$ | H | H |
| 230. | 248. | 266. | 284. | C$_6$H$_{13}$ | H | F |
| 231. | 249. | 267. | 285. | C$_6$H$_{13}$ | F | F |
| 232. | 250. | 268. | 286. | C$_7$H$_{15}$ | H | H |
| 233. | 251. | 269. | 287. | C$_7$H$_{15}$ | H | F |
| 234. | 252. | 270. | 288. | C$_7$H$_{15}$ | F | F |

Example 289

The following compound according to the invention is obtained analogously to Example 73 using the corresponding precursor:

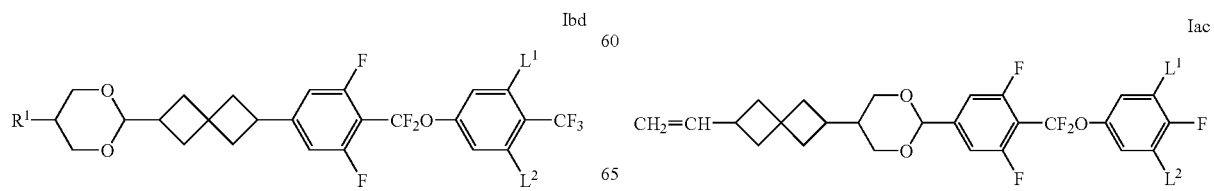

Iac

In detail, the synthesis is carried out as follows.

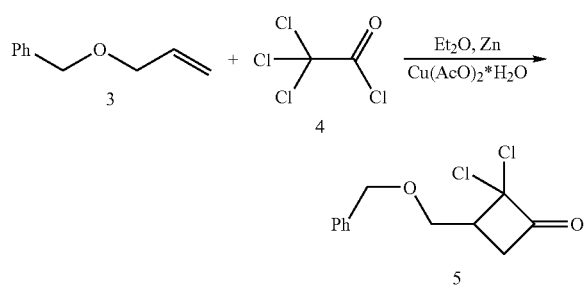

346 ml (3.00 mol) of 1-pentene are dissolved in 3 l of diethyl ether, and 315 g (4.83 mol) of zinc and 15 g (80 mmol) of copper(II) acetate monohydrate are added. 70 ml (3.30 mol) of trichloroacetyl chloride are subsequently added dropwise to the batch, during which the reaction mixture begins to boil. After 24 h at room temp., the solids are separated off, and the filtrate is washed with water, evaporated and passed through silica gel (pen/DCM 3:2), giving 365 g of a yellow oil (content: 64%).

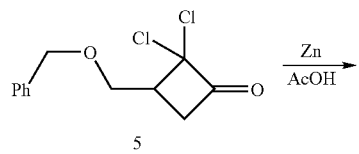

430 mmol of the chlorinated cyclobutanone 7 (100 g (content 77%)) are dissolved in 500 ml of acetic acid, and 100 g (1.5 mol) of zinc are added in portions at such a rate that a temperature of 80° C. is not exceeded. When the addition is complete, the batch is held at 80° C. for a further 2 h. After cooling to room temp., the batch is stirred with 500 ml of water and extracted with MTB ether. The combined organic phases are washed with water and sat. sodium hydrogencarbonate soln., dried over sodium sulfate and evaporated, giving 45.1 g of a yellow oil (content 78.7%).

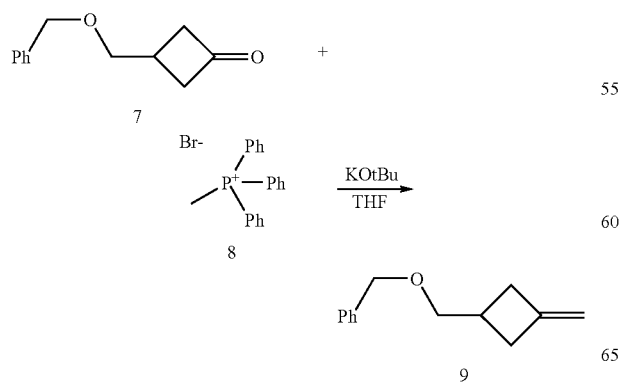

930 g (2.6 mol) of the Wittig salt 10 and 292 g of the ketone 8 are suspended in 2.5 l of THF, and 292 g (2.6 mol) of potassium tert-butoxide are added in portions at a temperature below 20° C. The batch is stirred overnight at room temp. After addition of water, the mixture is acidified using hydrochloric acid and extracted with n-pentane. The organic phase is evaporated and filtered through silica gel with n-pentane, giving 100.7 g (content 30%) of a yellow liquid.

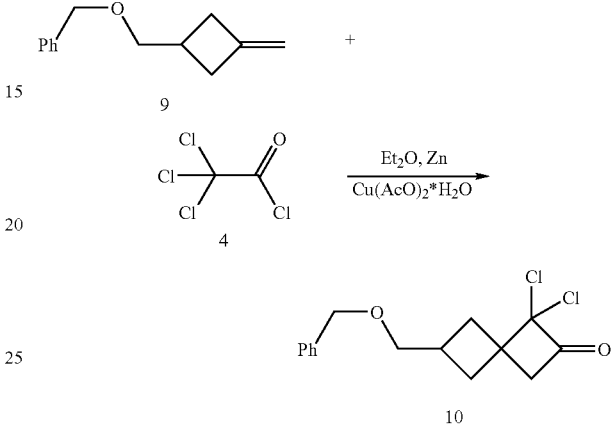

The ketone 10 is prepared analogously to the above procedure.

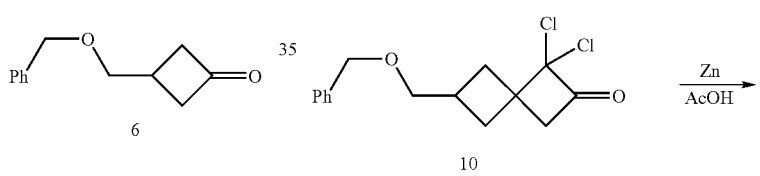

The dechlorination to give the ketone 11 is carried out analogously to the above procedure.

E. V. Dehmlow, S. Bueker *Chem. Ber.* 1993, 126, 2759-2764, describes vinyl acetate as starting material for the synthesis of a cyclobutyl ring. Compounds of type 1 are prepared in this way via the synthesis described.

$^1$H-NMR (CDCl$_3$, TMS): 7.33 (s, 5H, Ph-); 4.52 (s, 2H, Ph-CH$_2$—O); 3.46 (d, J=6.5 Hz, 2H, O—CH$_2$-cyclobutyl), 3.10 and 2.98 (2 m, 4H, 1-H$_2$ and 3-H$_2$); 2.60 (m$_c$, 1H 6-H); 2.29 and 2.06 (2m$_c$, 4H, 5-H$_2$ and 7-H$_2$).

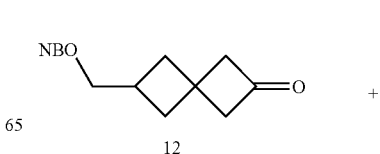

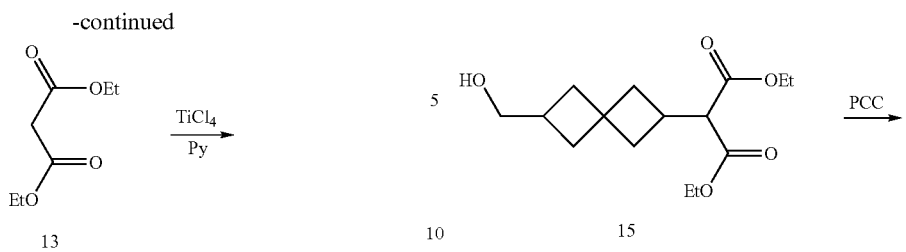

37.5 ml (340 mmol) of titanium tetrachloride are added to 200 ml of THF and 600 ml of dichloromethane at a temp. of −10° C. to −2° C. 28.6 ml (190 mmol) of diethyl malonate (13) and 50.0 g (86.5%, 190 mmol) of the ketone 12 are subsequently added to the reaction solution at −10° C. 55 ml (546 mmol) of pyridine are added dropwise to the batch at a temp. below −2° C. After 18 h at room temp., 1500 ml of water are added to the reaction mixture. The organic phase is washed with water and evaporated. The residue is filtered through silica gel (toluene/MTB ether 9:1), giving 54.8 g (75% purity; 59%) of the ester 14.

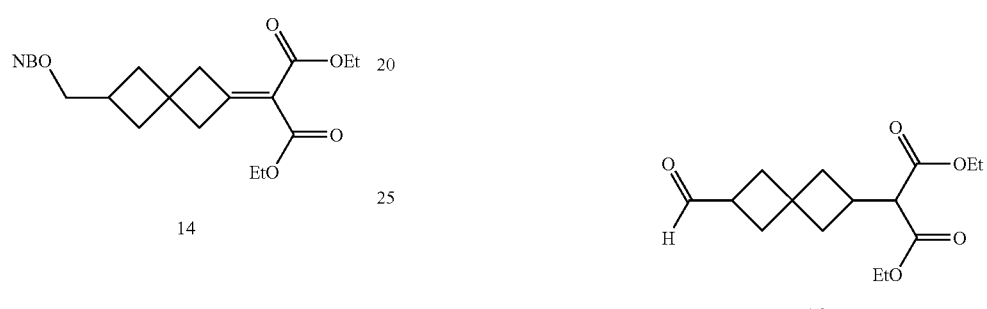

54.8 g (75% purity, 110 mmol) of the diester 14 are hydrogenated on a palladium catalyst in THF. The catalyst is separated off, and the solution is evaporated. The residue obtained is employed in the next step without further purification. 43.7 g (77% purity) of the saturated ester 15 are obtained.

30 g of PCC (140 mmol) and 30 g of Celite 545 are suspended in 300 ml of dichloromethane, and 43.2 g (77% purity, 120 mmol) of the alcohol 15, dissolved in 200 ml of dichloromethane, are added at T<25° C. The batch is stirred overnight. The filtrate of the suspension is evaporated, and the residue is passed through silica gel (n-pentane/MTB ether 4:1-1:1). The residue is employed in the subsequent step without further purification.

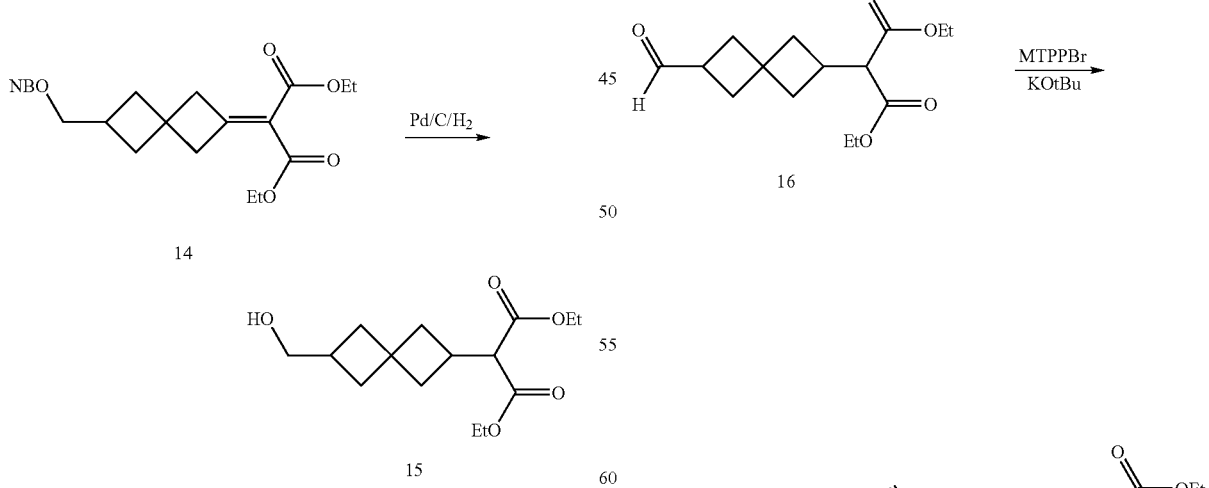

A solution of 7.2 g (60 mmol) of potassium tert-butoxide in 50 ml of THF is added to 24.7 g (70 mmol) of methyltriphenylphosphonium bromide at 0° C. After 15 min at this temperature, 13.0 g (50 mmol) of the aldehyde 16, dissolved in 50 ml of THF, are added. After 18 h at RT, water is added to the batch, and the mixture is adjusted to pH 6 using 1 N hydrochloric acid. The aqueous phase is extracted with MTB ether. The organic phase is washed with water, dried over sodium sulfate and evaporated. The residue is passed through silica gel (n-pentane/MTB ether 7:3). The residue is employed in the subsequent step without further purification.

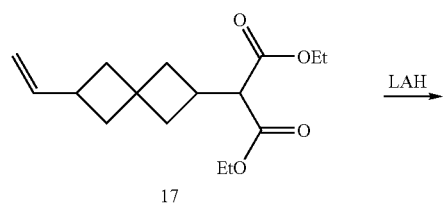

17

LAH →

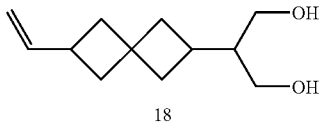

18

A solution of 18 g (70% purity, 60 mmol) of the malonate 17 in 50 ml of THF is added to a boiling suspension of 2.9 g (80 mmol) of lithium aluminium hydride in 50 ml of THF, and the mixture is subsequently kept under reflux for 1 h. The cooled batch is hydrolysed, acidified and diluted with MTB ether and filtered through Celite with suction. The organic phase is washed with water and sat. NaHCO$_3$ soln., dried and evaporated. The residue is employed in the subsequent step without further purification.

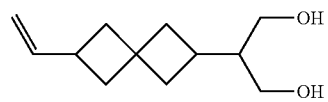

18

+

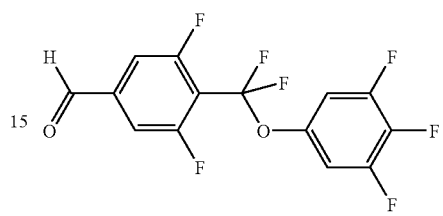

19 p-TsOH →

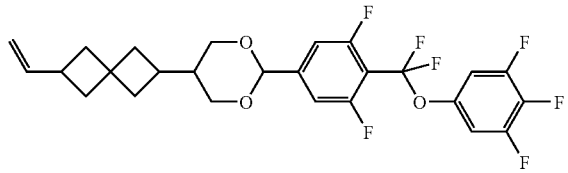

20

60 ml of toluene are added to 10 g (90% purity, 50 mmol) of the diol 18, 15.5 g (50 mmol) of the aldehyde 19 and 400 mg of p-toluenesulfonic acid, and the mixture is heated on a water separator for 1 h. The cooled batch is passed through silica gel (toluene). The product obtained is crystallised from n-heptane.

The product has the following properties:

C 75 N (54.3) I,

Δε=22.3 and

Δn=0.0964

Re. Example 78

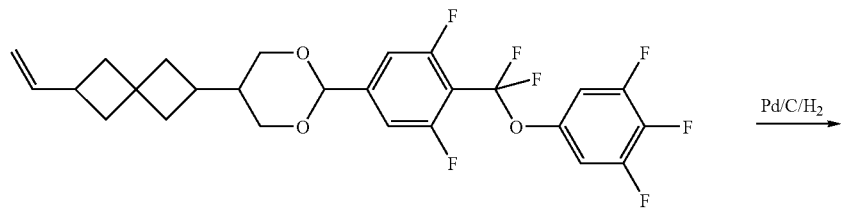

20

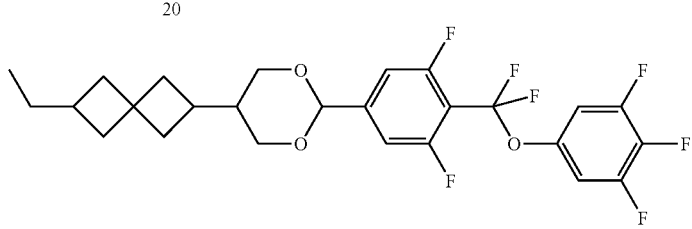

21

7.0 g (90% purity, 12 mmol) of the alkene 20 are dissolved in THF and hydrogenated on a palladium catalyst. The solution is subsequently evaporated, and the residue is passed through silica gel (toluene/n-heptane 1:1). Further purification by crystallisation from n-heptane. The product has the properties:

C 71 N (50.5) I,

Δ∈=23.9 and

Δn=0.0894.

Example 290

The preparation of the following compound is described as an example of a compound of the formula I having two nonpolar end groups (where $R^1$ and $R^2$ are both alkyl or alkenyl).

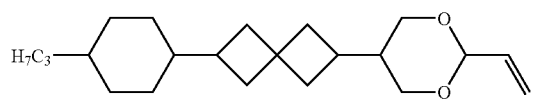

The precursor of the compound is obtained in accordance with the following reaction scheme.

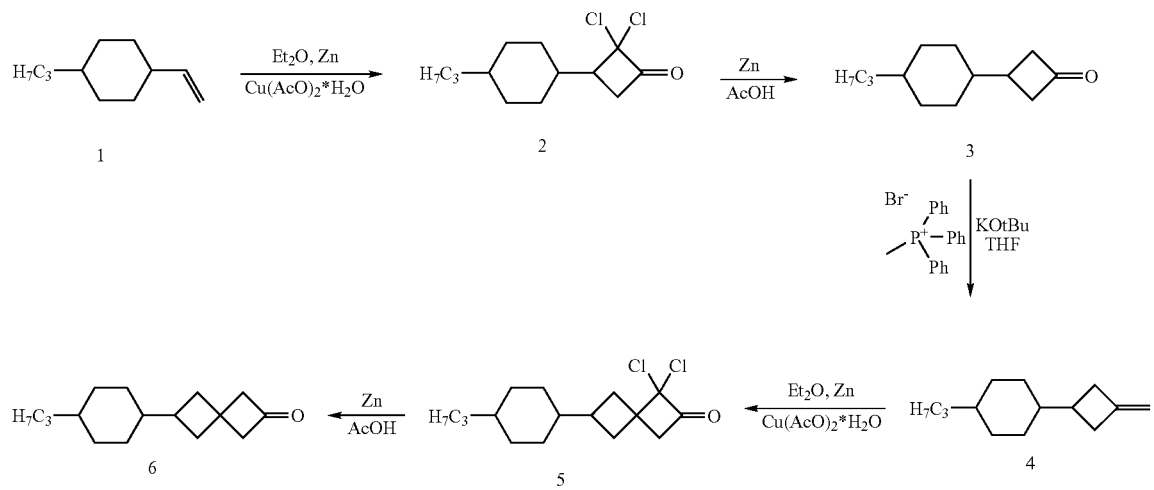

The further synthesis is carried out as follows.

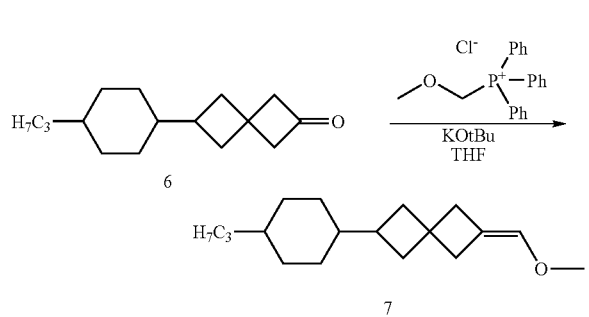

25 g (106 mmol) of the ketone 6 and 67.2 g (196 mmol) of methoxymethyltriphenylphosphonium chloride are suspended in 250 ml of THF, 11.9 g (106 mmol) of potassium tert-butoxide are added at T<20° C., and the mixture is stirred at RT for 18 h. Sat. ammonium chloride soln. is added to the batch, which is then diluted with 500 ml of n-heptane. The organic phase is evaporated, and the residue is passed through silica gel (n-heptane/toluene 1:1). The product is employed in the subsequent step without further purification.

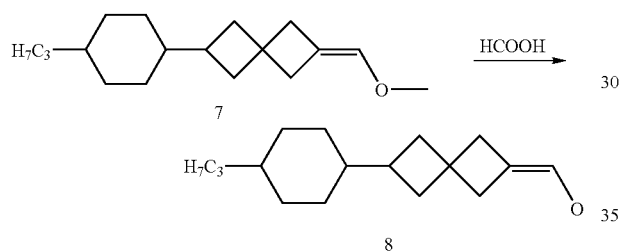

16 g of the product of the precursor are dissolved in 60 ml of toluene, 36 ml of formic acid are added, and the mixture is stirred at RT for 18 h. The batch is subsequently added to 200 ml of water. The aqueous phase is extracted with MTB ether, the organic phase is washed with sat. NaHCO₃ soln. and evaporated. The residue is employed in the subsequent step without further purification.

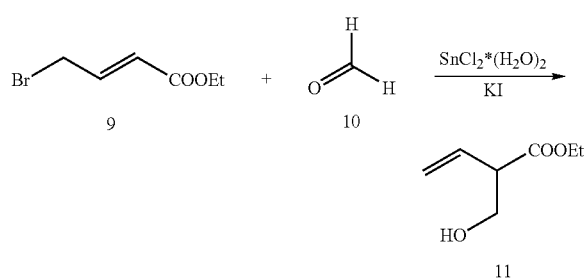

298 g (1.32 mol) of tin(II) chloride, 300 g (1.32 mol) of ethyl 4-bromo-crotonate and 438 g (2.64 mol) of potassium iodide are initially introduced in 3 l of water, and a 37% solution of formaldehyde in water is added at T<35° C. After 24 h, the batch is extracted with diethyl ether. The organic phase is evaporated and passed through silica gel (toluene, toluene/MTB ether 1:1). The residue is distilled in vacuo, b.p. 70° C.

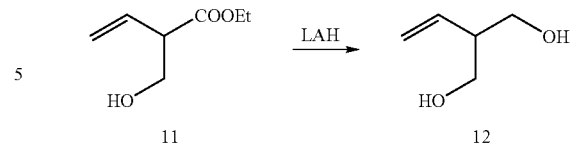

208 g (24% purity, 346 mmol) of the ester 11 are dissolved in toluene and added to a boiling suspension of 12.4 g (330 mmol) of lithium aluminium hydride in 100 ml of toluene and 1200 ml of THF. After heating under reflux for 1 h and subsequent cooling, the batch is hydrolysed, and a hot solution of 93.2 g of sodium bicarbonate decahydrate in 30 ml of water is added. After stirring for 30 min, the solid is separated off. The filtrate is evaporated. The residue is employed in the subsequent step without further purification.

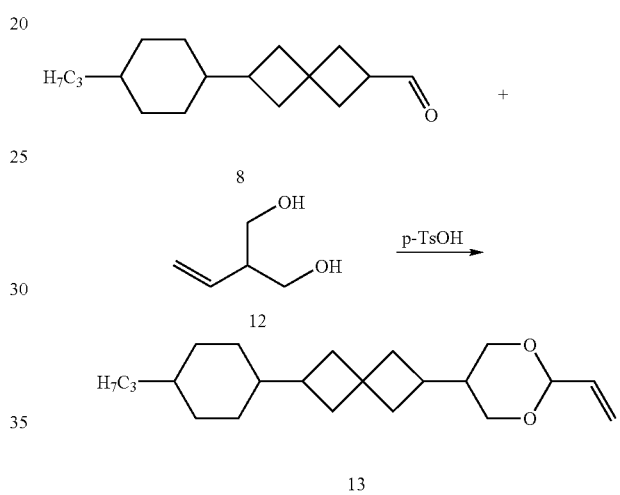

60 ml of toluene are added to 4.1 g (80% purity, 32 mmol) of the diol 12, 16.6 g (50% purity, 31 mmol) of the aldehyde 8 and 360 mg of p-toluenesulfonic acid, and the mixture is heated at the boil on a water separator for 1 h. The cooled batch is passed through silica gel (toluene), the eluate is evaporated, and the residue is crystallised from n-heptane, passed through basic AlO$_x$ (toluene/n-heptane 1:1) and re-crystallised from n-heptane.

The product has the properties:

C 40 S$_B$ 121 I,

Δ∈=0.8 and

Δn=0.0491.

The invention claimed is:
1. A dioxane compound according to formula I;

$$R^1\text{-}(A^1\text{-}Z^1)_m\text{-}G\text{-}(Z^2\text{-}A^2)_n\text{-}R^2 \qquad I$$

in which
G is

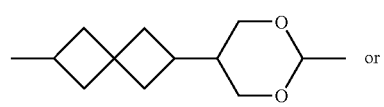 or

-continued

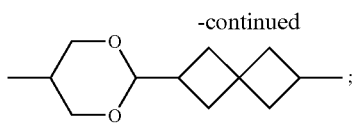

R¹ and R² are each, independently of one another, identically or differently, H, halogen, —CN, —SCN, —NCS, —SF₅, —SCF₃, —CF₃, —CF=CF₂, —CF₂CF₂CF₃, —OCF₃, —OCHF₂, —CF₂CH₂CF₃, —OCH₂CF₂CHFCF₃ or a linear or branched, optionally chiral alkyl or alkoxy radical having 1 to 15 C atoms which is unsubstituted, mono- or polysubstituted by halogen and in which one or more CH₂ groups are each optionally replaced, independently of one another, by —O—, —S—, —CO—, —CO—O—, —O—CO—, —O—CO—O—, —CH=CH—, —CH=CF—, —CF=CF—, —C≡C— or

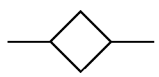

in such a way that heteroatoms are not linked directly to one another;

A¹ and A² are each, independently of one another, identically or differently,
  a) trans-1,4-cyclohexylene, in which, in addition, one or more non-adjacent CH₂ groups are each optionally replaced by —O— or —S— and in which, in addition, one or more H atoms are each optionally replaced by F,
  b) 1,4-phenylene, in which one or two CH groups are each optionally replaced by N and in which, in addition, one or more H atoms are each optionally replaced by halogen, —CN, —CH₃, —CHF₂, —CH₂F, —CF₃, —OCH₃, —OCHF₂ or —OCF₃,
  c) bicyclo[1.1.1]pentane-1,3-diyl, bicyclo[2.2.2]octane-1,4-diyl, spiro-[3.3]heptane-2,6-diyl, naphthalene-2,6-diyl, naphthalene-2,7-diyl, decahydronaphthalene-2,6-diyl, 1,2,3,4-tetrahydronaphthalene-2,6-diyl, piperidine-1,4-diyl, phenanthrene-2,7-diyl, fluorene-2,7-diyl, anthracene-2,6-diyl, anthracene-2,7-diyl, or indane-2,5-diyl, where in each case one H atom or a plurality of H atoms are each optionally replaced by halogen,
  d) 1,4-cyclohexenylene or 1,3-cyclobutane-1,3-diyl;

Z¹ and Z² are each, independently of one another, identically or differently, —O—, —CH₂O—, —OCH₂—, —CO—O—, —O—CO—, —CF₂O—, —OCF₂—, —CF₂=CF₂—, —CH₂=CF₂—, —CF₂CH₂—, —CH₂CH₂—, —CH=CH—, —CH=CF—, —CF=CH—, —CF=CF—, —CF=CF—COO—, —O—CO—CF=CF—, —C≡C—, —CH₂CH₂CF₂O—, or a single bond;

m is 0, 1, 2 or 3; and
n is 1, 2, or 3;
wherein the Z² bridge group attached to group G is a single bond.

2. A compound according to claim 1, wherein m is 0, 1 or 2, and n is 1 or 2.

3. A compound according to claim 1, wherein m is 0 or 1, and n is 1 or 2.

4. A compound according to claim 1, wherein G is

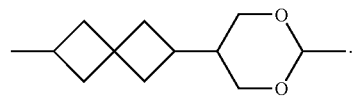

5. A compound according to claim 1, wherein G is

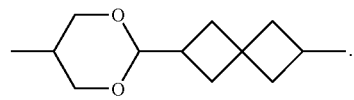

6. A compound according to claim 1, wherein said compound is of one of the following formulae:

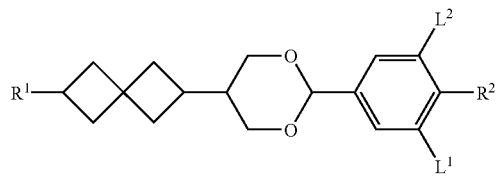

Iaa

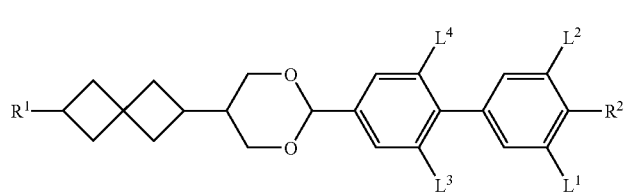

Iab

-continued
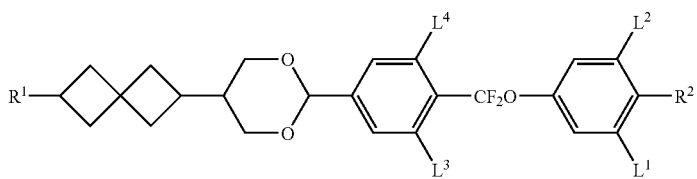
Iac
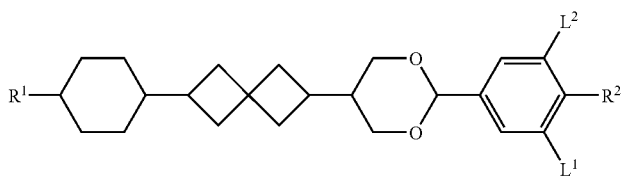
Iad
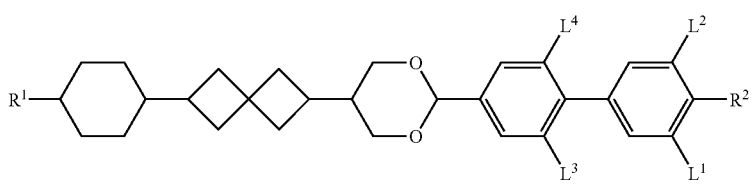
Iae
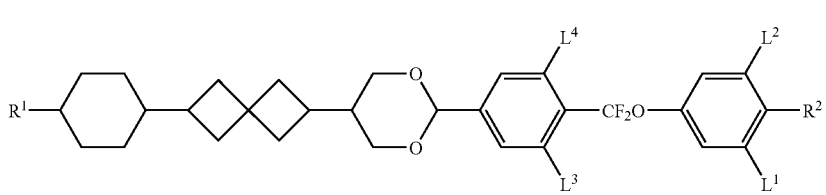
Iaf
in which $L^1$, $L^2$, $L^3$ and $L^4$ independently of one another, identically or differently, are each H or F.
7. A compound according to claim 1, wherein said compound is of one of the following formulae:
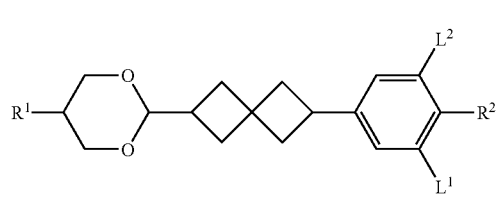
Iba
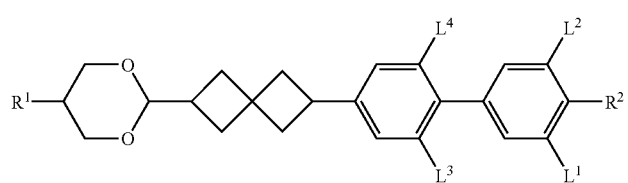
Ibb
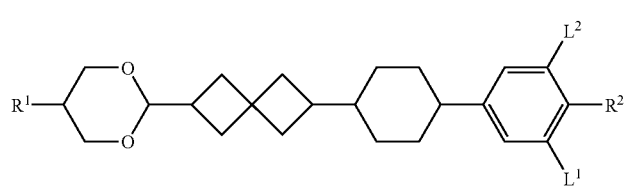
Ibc -continued

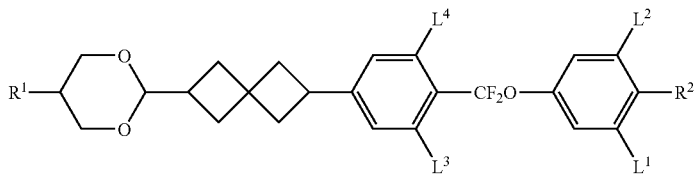
Ibd

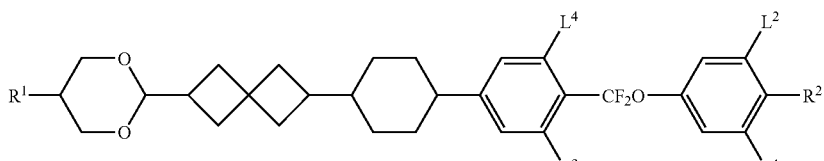
Ibe

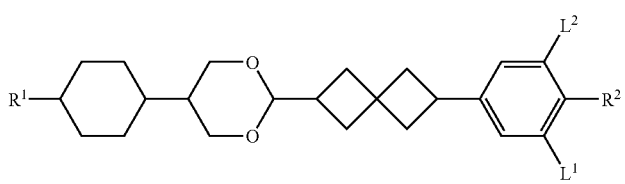
Ibf

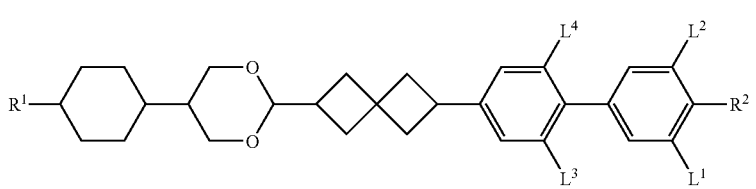
Ibg

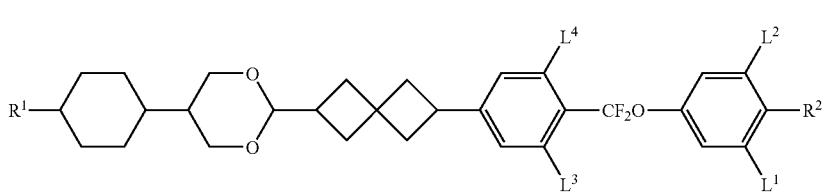
Ibh in which $L^1$, $L^2$, $L^3$ and $L^4$, independently of one another, identically or differently, are each H or F.

8. A compound according to claim 1, wherein $R^1$ is H or a linear alkyl radical having 1 to 10 C atoms.

9. A compound according to claim 1, wherein $R^2$ is H, a linear alkoxy radical having 1 to 10 C atoms, —F, —Cl, —CF$_3$, —OCF$_3$, —OCHF$_2$, —CN, —NCS, or —SF$_5$.

10. A liquid-crystalline medium having at least two liquid-crystalline components, wherein said medium at least one compound according to claim 1.

11. A liquid-crystal display element, comprising a liquid-crystalline medium according to claim 10.

12. A reflective or transflective liquid-crystal display element, comprising a liquid-crystalline medium according to claim 10.

13. An electro-optical display element, comprising a liquid-crystalline medium according to claim 10.

14. A spirodiol compound of the following formula

wherein $R^1$ is H, halogen, —CN, —SCN, —NCS, —SF$_5$, —SCF$_3$, —CF$_3$, —CF=CF$_2$, —CF$_2$=CF$_2$CF$_3$, —OCF$_3$, —OCHF$_2$, —CF$_2$CH$_2$CF$_3$, —OCH$_2$CF$_2$CHFCF$_3$ or a linear or branched, optionally chiral alkyl or alkoxy radical having 1 to 15 C atoms which is unsubstituted, mono- or polysubstituted by halogen and in which one or more CH$_2$ groups are each optionally replaced, independently of one another, by —O—, —S—, —CO—, —CO—O—, —O—CO—, —O—CO—O—, —CH=CH—, —CH=CF—, —CF=CF—, —C≡C— or

in such a way that heteroatoms are not linked directly to one another;

$A^1$ is a) trans-1,4-cyclohexylene, in which, in addition, one or more non-adjacent CH$_2$ groups are each optionally replaced by —O— or —S— and in which, in addition, one or more H atoms are each optionally replaced by F, b) 1,4-phenylene, in which one or two CH groups are each optionally replaced by N and in which, in addition, one or more H atoms are each optionally replaced by halogen, —CN, —CH$_3$, —CHF$_2$, —CH$_2$F, —CF$_3$, —OCH$_3$, —OCHF$_2$ or —OCF$_3$, c) bicyclo[1.1.1]pentane-1,3-diyl, bicyclo[2.2.2]octane-1,4-diyl, spiro-[3.3]heptane-2,6-diyl, naphthalene-2,6-diyl, naphthalene-2,7-diyl, decahydronaphthalene-2,6-diyl, 1,2,3,4-tetrahydronaphthalene-2,6-diyl, piperidine-1,4-diyl, phenanthrene-2,7-diyl, fluorene-2,7-diyl, anthracene-2,6-diyl, anthracene-2,7-diyl, or indane-2,5-diyl, where in each case one H atom or a plurality of H atoms are each optionally replaced by halogen, d) 1,4-cyclohexenylene or 1,3-cyclobutane-1,3-diyl;

$Z^1$ is —O—, —CH$_2$O—, —OCH$_2$—, —CO—O—, —O—CO—, —CF$_2$O—, —OCF$_2$—, —CF$_2$=CF$_2$—, —CH$_2$CF$_2$—, —CF$_2$CH$_2$—, —CH$_2$CH$_2$—, —CH=CH—, —CH=CF—, —CF=CH—, —CF=CF—, —CF=CF—COO—, —O—CO—CF=CF—, —C≡C—, —CH$_2$CH$_2$CF$_2$O—, or a single bond; and m is 1, 2 or 3.

15. A process for the preparation of a compound according to claim 1, said process comprising:

(a) reacting a spirodiol of the following formula

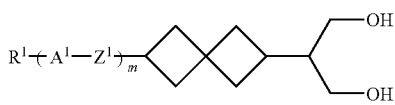

with a compound of the formula

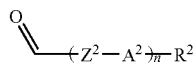

to obtain a compound of the following formula

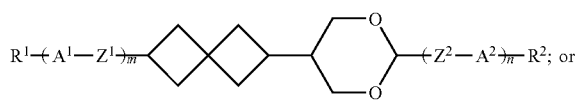

(b) reacting a spirodiol of the following formula

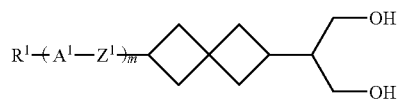

with chlorotrimethylsilane to obtain a compound of the formula

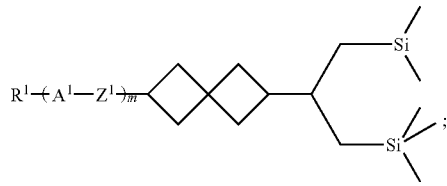

and then reacting the compound of the formula

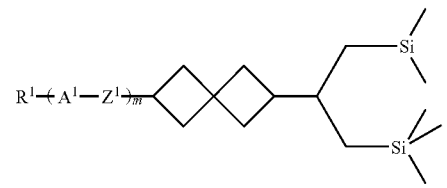

with a compound of the formula

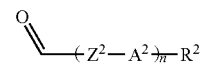

to obtain a compound of the following formula

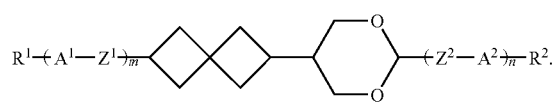

16. In an method of generating an electro-optical effect using an electro-optical display element, the improvement wherein said electro-optical display element contains, as dielectric, a liquid-crystalline medium comprising a compound according to claim 1.

17. A compound according to claim 1, wherein $Z^1$ is —CH$_2$CH$_2$—, —CH=CH—, —C≡C—, —CF$_2$=CF$_2$—, —CF=CF—, —CF$_2$O—, —OCF$_2$— or a single bond.

18. A compound according to claim 17, wherein $Z^1$ is a single bond.

19. A compound according to claim 1, wherein n is 2 or 3, and the bridge groups $Z^2$, that are not attached to group G, are each —CH$_2$CH$_2$—, —CH=CH—, —C≡C—, —CF$_2$=CF$_2$—, —CF=CF—, —CF$_2$O—, —OCF$_2$—, or a single bond.

20. A compound according to claim 19, wherein the bridge groups $Z^2$ not attached to group G are each —CF$_2$O— or a single bond.

21. A compound according to claim 1, wherein $A^1$ and $A^2$ are each independently Phe, Cyc, Che, Pyd, Pyr or Dio, Phe is a 1,4-phenylene radical which is unsubstituted or mono- or polysubstituted by CH$_3$, Cl, F or CN, Cyc is a 1,4-cyclohexylene radical which is unsubstituted or mono- or polysubstituted by CH$_3$, Cl, F or CN, Che is a 1,4-cyclohexenylene radical, Pyd is a pyridine-2,5-diyl radical,
Pyr is a pyrimidine-2,5-diyl radical, and
Dio is a 1,3-dioxane-2,5-diyl radical.

22. A compound according to claim 21, wherein $A^1$ and $A^2$ are each independently Phe or Cyc.

23. A compound according to claim 6, wherein $R^1$ is H, linear alkyl having 1 to 10 C atoms, alkoxy radical having 1 to 10 C atoms, alkenyl having 2 to 10 C atoms, or alkenyloxy having 2 to 10 C atoms.

24. A compound according to claim 7, wherein $R^1$ is H, linear alkyl having 1 to 10 C atoms, alkoxy radical having 1 to 10 C atoms, alkenyl having 2 to 10 C atoms, or alkenyloxy having 2 to 10 C atoms.

25. A compound according to claim 6, wherein $R^2$ denotes —F, —$CF_3$, —$OCF_3$ or —CN.

26. A compound according to claim 7, wherein $R^2$ denotes —F, —$CF_3$, —$OCF_3$ or —CN.

27. A compound according to claim 6, wherein said compound is selected from the following formulae:

Iaa1
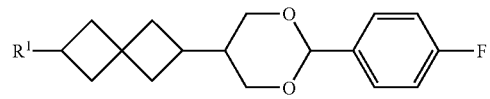

Iaa2
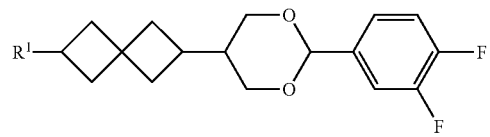

Iaa3
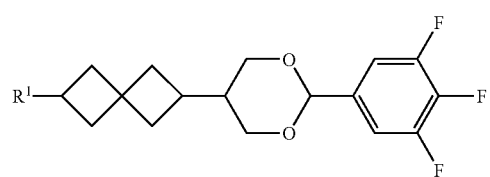

Iaa4
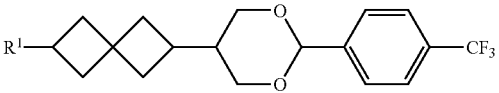

Iaa5
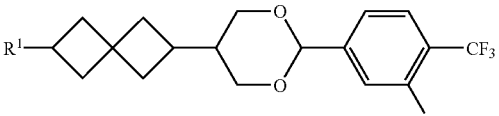

Iaa6
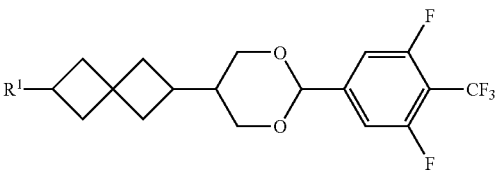

Iaa7
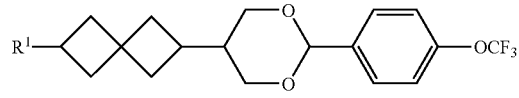

Iaa8
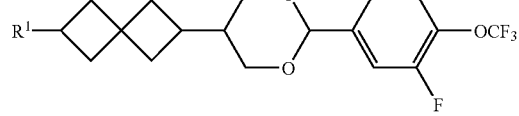

-continued

Iaa9
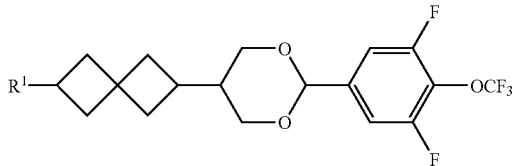

Iac1
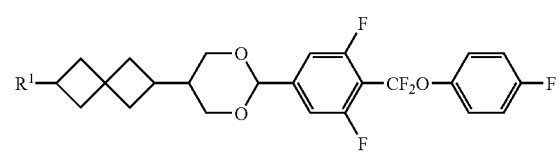

Iac2
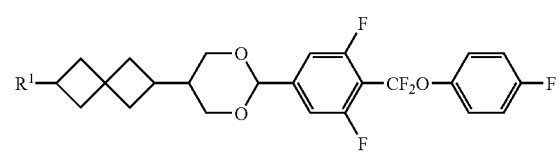

Iac3
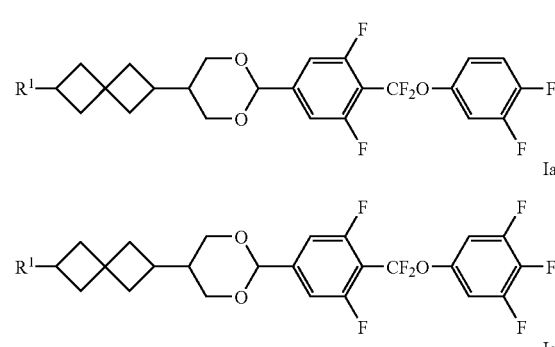

Iac4
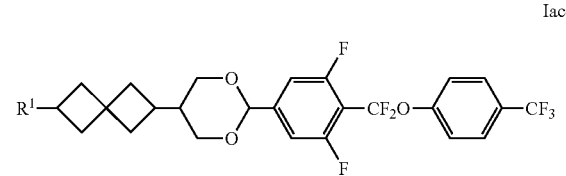

Iac5
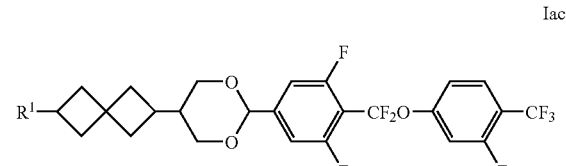

Iac6
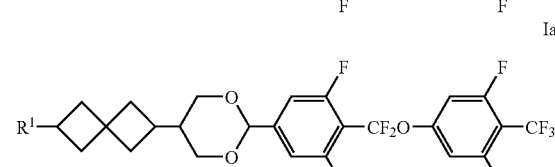

Iac7
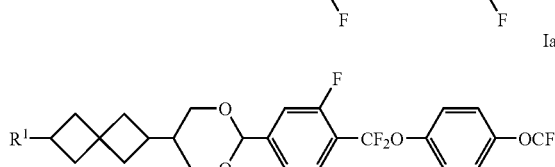

Iac8
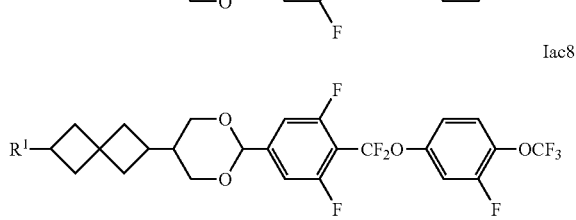

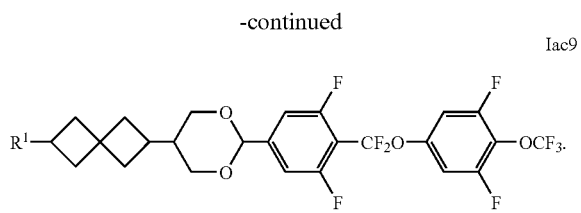
28. A compound according to claim 7, wherein said compound is selected from the following formulae:
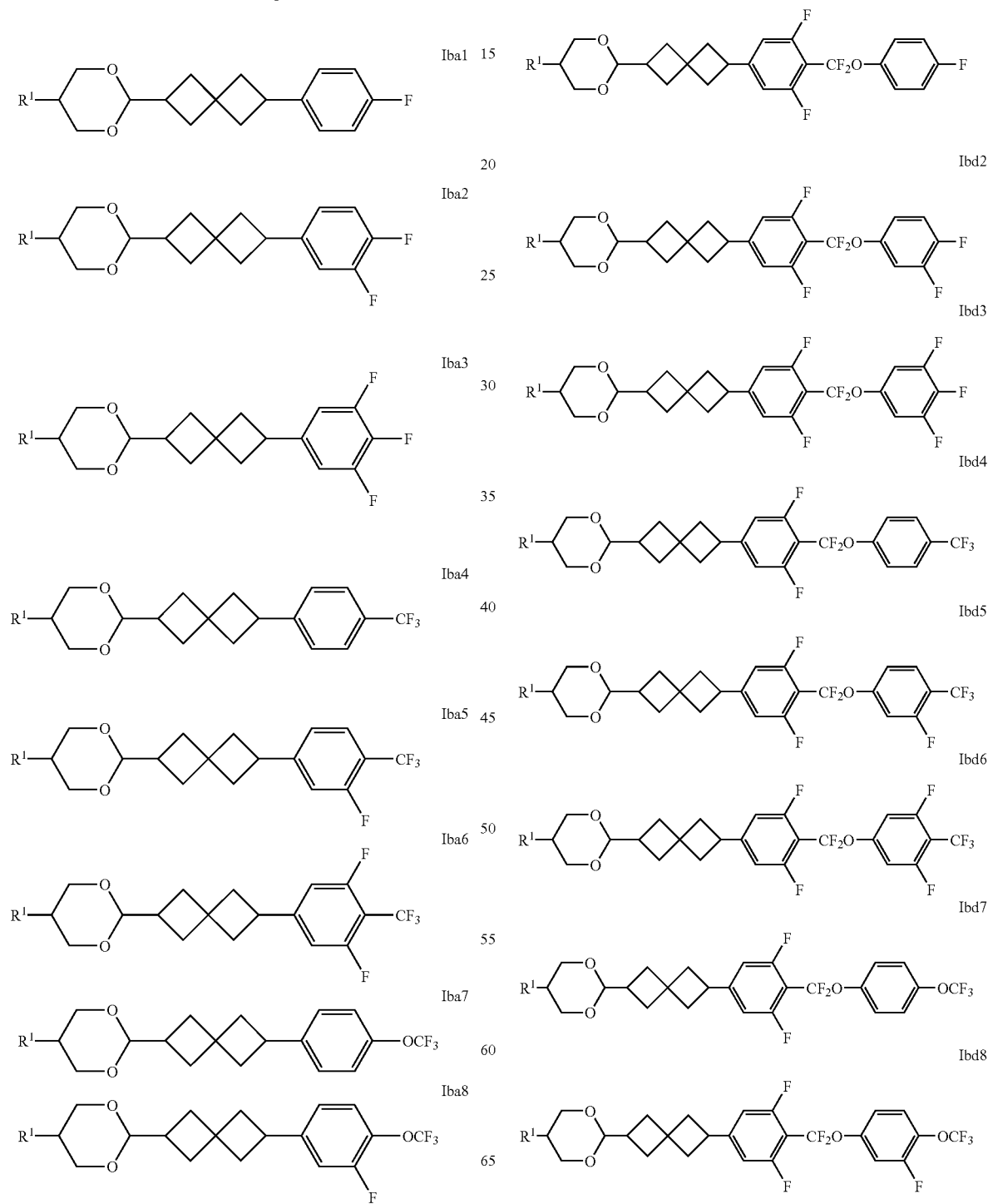

-continued
Ibd9
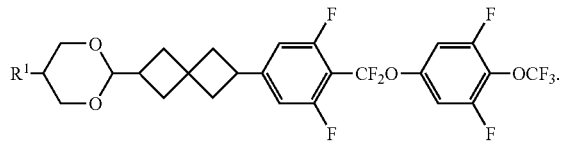
29. A compound according to claim 27, wherein $R^1$ is H, linear alkyl having 1 to 10 C atoms, alkoxy radical having 1 to 10 C atoms, alkenyl having 2 to 10 C atoms, or alkenyloxy having 2 to 10 C atoms.
30. A compound according to claim 29, wherein $R^1$ is H, linear alkyl having 1 to 10 C atoms, alkoxy radical having 1 to 10 C atoms, alkenyl having 2 to 10 C atoms, or alkenyloxy having 2 to 10 C atoms.
* * * * *

UNITED STATES PATENT AND TRADEMARK OFFICE
CERTIFICATE OF CORRECTION

PATENT NO. : 7,691,456 B2  Page 1 of 1
APPLICATION NO. : 12/089257
DATED : April 6, 2010
INVENTOR(S) : Lietzau et al.

It is certified that error appears in the above-identified patent and that said Letters Patent is hereby corrected as shown below:

Column 48, line 42 reads: "$-CF_3, -CF=CF_2, -CF_2=CF_2CF_3, -OCF_3,$" should read: -- $-CF_3, -CF=CF_2, CF_2CF_2CF_3, -OCF_3$ --

Column 49, line 17 reads: "$-O-CO-, -CF_2O, -OCF_2, -CF_2=CF_2-$" should read: -- $-O-CO-, -CF_2O, -OCF_2, -CF_2CF_2-$ --

Column 50, line 54 reads: "$-CF_2=CF_2, -CF=CF-, -CF_2O-, -OCF_2-,$ or a" should read: -- $-CF_2CF_2, -CF=CF-, -CF_2O-, -OCF_2-,$ or a --

Signed and Sealed this

Twelfth Day of October, 2010

David J. Kappos
*Director of the United States Patent and Trademark Office*